US009968650B2

United States Patent
Zlotnick et al.

(10) Patent No.: US 9,968,650 B2
(45) Date of Patent: May 15, 2018

(54) MODIFIED VIRAL STRUCTURAL PROTEIN WITH ANTIVIRAL ACTIVITY

(75) Inventors: Adam Zlotnick, Bloomington, IN (US); Dan Loeb, Madison, WI (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days. days.

(21) Appl. No.: 14/232,377

(22) PCT Filed: Jul. 13, 2012

(86) PCT No.: PCT/US2012/046642
§ 371 (c)(1),
(2), (4) Date: Jan. 13, 2014

(87) PCT Pub. No.: WO2013/010069
PCT Pub. Date: Jan. 17, 2013

(65) Prior Publication Data
US 2014/0148381 A1   May 29, 2014

Related U.S. Application Data

(60) Provisional application No. 61/507,269, filed on Jul. 13, 2011.

(51) Int. Cl.
| | | |
|---|---|---|
| *A61K 38/16* | (2006.01) | |
| *A01K 67/027* | (2006.01) | |
| *C07K 14/005* | (2006.01) | |
| *G01N 33/569* | (2006.01) | |
| *A61K 38/00* | (2006.01) | |

(52) U.S. Cl.
CPC .......... *A61K 38/162* (2013.01); *A01K 67/027* (2013.01); *C07K 14/005* (2013.01); *G01N 33/56983* (2013.01); *A01K 2207/05* (2013.01); *A01K 2267/0337* (2013.01); *A61K 38/00* (2013.01); *C12N 2730/10122* (2013.01); *C12N 2730/10133* (2013.01); *C12N 2740/16222* (2013.01); *C12N 2799/025* (2013.01)

(58) Field of Classification Search
None
See application file for complete search history.

(56) References Cited

PUBLICATIONS

Blair et al. HIV Capsid is a Tractable Target for Small Molecule Therapeutic Intervention. PLoS Pathog. Dec. 2010; 6(12): 1-10.*
Baker et al., Protein Structure Predication and Structural Genomics, Science (2001) vol. 294, No. 5540, pp. 93-96.*
Attwood, T. The Babel of Bioinformatics, Science (2000) vol. 290, No. 5491, pp. 471-473.*
Tan et al., 'HAP mimic hepatitis B virus core mutation leads to aggressive capsid assembly'; 2010 Cancer Research Day Abstract book, Poster No. 23, Indiana University (2010).
International Search Report and Written Opinion dated Jan. 17, 2013 from the International Searching Authority in priority application No. PCT/US2012/046642.
IPRP dated Jan. 14, 2014 from the International Searching Authority in priority application No. PCT/US2012/046642.
Tan et al., "HAP mimic hepatitis B virus core mutation leads to aggressive capsid assembly" 2010 Cancer Research Day Abstract book, Poster No. 23, Indiana University (2010).
Newman et al., "Stability and morphology comparisons of self-assembled virus-like particles from wild-type and mutant human hepatitis B virus capsid proteins", Journal of Virology, vol. 77, No. 24, pp. 12950-12960 (Dec. 2003).
Bourne et al., "A mutant Hepatitus B virus core protein mimics inhibitors of icosahedral capsid self-assembly", B-(iochemistry, vol. 48, pp. 1736-1742 (Feb. 5, 2009).
Zlotnick, "Antiviral HBV assembly effectors (AEs): mechanisms and implications for eradication", Global Antiviral Journal, vol. 7, Supple. 1: HEP DART 2011: Frontiers in drug development for viral hepatitis, p. 28, Abstract 22 (Dec. 4-8, 2011).
Ganser-Pronillos et al. 2008. The structural biology of HIV assembly. *Curr Opin Struct Biol* 18:203-217, emphasis added.
PDB accession codes 3P0A, 3H47, 3MGE, 4QNB, 3GV2.
Pornillos et al. 2009. X-ray structures of the hexameric building block of the HIV capsid. *Cell* 137:1282-1291.
Data et al. 2011. On the role of the SP1 domain in HIV-1 particle assembly: a molecular switch? *Journal of Virology* 85:4111-4121.

* cited by examiner

*Primary Examiner* — Michelle S Horning
(74) *Attorney, Agent, or Firm* — Faegre Baker Daniels LLP

(57) ABSTRACT

This disclosure provides a novel strategy to cope with chronic virus infection by introducing a dominant negative viral structural protein to disturb effective virion production. The dominant negative structural protein mimics antiviral drugs through structural and biochemical interactions during virus assembly. An effective gene therapy model for chronic viral infected diseases is proposed in this disclosure, as represented by HBV Cpdominant1 to clear viral infection.

10 Claims, 17 Drawing Sheets

(the above figure shows the light scattering traces.)

US 9,968,650 B2

MODIFIED VIRAL STRUCTURAL PROTEIN WITH ANTIVIRAL ACTIVITY

CROSS-REFERENCE TO RELATED APPLICATIONS

This application is a US National Phase filing of PCT/US2012/046642, filed on Jul. 13, 2012, which claims benefit of U.S. 61/507,269, filed on Jul. 13, 2011. The disclosure of which is expressly incorporated entirely by reference.

GOVERNMENT SUPPORT CLAUSE

This invention was made with government support under AI067417 and CA022443 awarded by the National Institutes of Health. The Government has certain rights in the invention.

FIELD OF INVENTION

This invention relates to modified viral structural proteins that inhibit viral activity and are thus applicable for gene therapy for virus infected chronic diseases. Specifically, it embraces modified viral structural proteins in viruses that inhibit effective virion assembly.

BACKGROUND

Virus particles (known as virions) consist of two or three parts: the genetic material made from either DNA or RNA, molecules that carry genetic information; a protein coat that protects these genes; and in some cases, an envelope of lipids that surrounds the protein coat when they are outside a cell. The shapes of viruses range from simple helical and icosahedral forms to more complex structures. Virions may also include other accessory proteins of viral or host origin.

Viral infections in animals provoke an immune response that usually eliminates the infecting virus. Immune responses can also be produced by vaccines, which confer an artificially acquired immunity to the specific viral infection. However, some viruses including those causing AIDS and viral hepatitis evade these immune responses or persist in spite of them and result in chronic infections. Antibiotics have no effect on viruses, but several antiviral drugs have been developed.

Antiviral drugs are often nucleoside analogues (mimics of DNA building-blocks), which viral RNA or DNA polymerases mistakenly incorporate into their genomes during replication. The life-cycle of the virus is then halted because the newly synthesized DNA is inactive. This is because these analogues lack the hydroxyl groups, which, along with phosphorus atoms, link together to form the strong "backbone" of the DNA molecule. This is called DNA chain termination. Examples of nucleoside analogues are ACICLOVIR® for Herpes simplex virus, one of the oldest and most frequently prescribed antiviral drugs. Other nucleoside analogs such as LAMIVUDINE® target a different polymerase, reverse transcriptase, of HIV and Hepatitis B virus. Other antiviral drugs target different stages of the viral life cycle. For example, HIV is dependent on a proteolytic enzyme called the HIV-1 protease for it to become fully infectious. There is a large class of drugs called protease inhibitors that inactivate this enzyme. All of these drugs affect enzymes, biochemical catalysts, that are mechanistically similar to human enzymes, resulting in cross-reactivity.

Chronic hepatitis B virus infection poses great health risks to a large population. Approximately 360 million people suffer from chronic HBV. Chronic HBV contributes to about 600,000 deaths each year, about one third from hepatocellular carcinoma. More than 100 million chronically infected people live in the People's Republic of China, more than 1 million live in the United States. In a chronically infected individual, up to 95% of hepatocytes are infected. Few people recover from chronic infections. Chronic HBV is often treated with nucleoside analogs such as LAMIVUDINE®, ENTACAVIR®, or TENOFOVIR®.

Despite the palliative therapeutics available so far, there is no reliable cure for chronic viral infections. Once initiated, treatment of HBV with nucleoside analogs may be lifelong to prevent viral rebound, which can be life threatening. However, long term treatment is expensive and raises its own issues. Repeated administration of antiviral drugs may cause side effects and may lead to the emergence of drug resistant HBV mutants. Because of extensive gene overlap in HBV, some mutants are insensitive to the modern recombinant HBV vaccine. The vaccine, which has been in use for approximately two decades, is protective but not therapeutic for existing infections.

Therefore, there remains the need to develop an effective anti-viral strategy to cope with the challenges that chronic viruses such as HBV and also HIV pose to existing therapeutics.

SUMMARY

This disclosure provides a modified viral structural protein that has faster self-assembly rates and stronger self-association than the wild type protein. The modified viral structural protein co-assembles with the wild type protein faster than the wild type proteins counterparts, leading to deviant assembly products: defective or empty viral particles.

In some embodiment the modified viral structural protein is constitutively active for self-assembly and it alters the kinetics of assembling of wild type viral structural protein in the absence of viral assembly signal by enhancing the assembly rates (a kinetic effect) and stabilizing intermediates and the resulting complex (a thermodynamic effect). By altering assembly kinetics and stabilizing co-assembled capsids, the modified viral structural protein induces the assembly of capsid protein in the absence of viral assembly signal.

In some embodiment the modified viral structural protein is resistant to antiviral compound heteroaryldihydropyridines (HAPs) but displays HAP antiviral effects directed to HBV.

In some embodiment the modified viral structural protein is from one of the following viruses: HBV or HIV.

In some embodiment the modified HBV viral structural protein is built from a wildtype HBV core protein with a truncation at residue 172 or 176 so that the resultant dominant negative HBV core protein supports HBV RNA reverse transcription but is distinguable from the full length wild type HBV core protein in size.

In some embodiment the modified HIV structural protein incorporates assembly-activing mutations in HIV's CA and/or SP1 domains.

In some embodiment the modified viral structural protein is selected from the group consisting of the following RNA virus families: Flavivirdae (including HCV, Dengue Fever Virus, and West Nile Virus), and Togaviridae (including WEE, VEE, Chikungunya, and sindbis virus)

In some embodiment the modified viral structural protein is selected from the group consisting of the following DNA virus families: herpesviridae and papillomaviridae. For example, in herpesviridae family the candidates are herpes simplex 1, herpes simplex 2, herpes Zoster (chicken pox and shingles), and Kaposi's sarcoma herpesvirus; in the papilomaviridae family HPV 16 is a possible candidate.

In one preferred embodiment the modified viral structural protein is HBV Cpdominant1 as set in SEQ. ID. NO: 1 (HBV Cpdominant1 V124W).

In another preferred embodiment the modified viral structural protein is HBV Cp selected from the group consisting of SEQ. ID. NOs: 2-39.

This disclosure provides a gene therapy model to treat a wild type virus-infected living system. Specifically, the gene therapy model includes the following steps: a. providing living systems infected with a wild type virus; b. as a control, providing an organ (or tissue) specific vector containing no extrageneous nucleotide sequence (empty vector) and transfecting the empty vector into at least one group of the wild type virus-infected living system; c. constructing the organ specific vector that properly expresses the mutant of the virus core protein (dominant negative mutant) and transfecting the organ specific vector containing the dominant negative mutant into yet another group of wild type virus-infected living system; d. measuring effective viral production in the living systems from step b and step c; and e. comparing the effective viral production in empty vector treated system versus dominant negative treated system.

In one preferred embodiment the living system in the gene therapy model is a hepatoma cell line, such as HepG2. The virus is HBV and the dominant negative mutant is HBV Cpdominant1 as set forth in SEQ. ID. NO: 40 that contains nucleotide sequence of HBV Cpdominant1.

In another preferred embodiment the living system in the gene therapy model is a mouse.

In another preferred embodiment the living system in the gene therapy model is a human.

In one preferred embodiment the organ specific vector used in the gene therapy model is hepatotropic adeno-associated virus (AAV).

In another preferred embodiment the hepatotropic vector is an Adeno-associated virus with a self-complementary genome.

This disclosure also provides a. method to identify dominant negative virus mutations that demonstrate accelerated self-assembly in the absence of viral assembly signal to provide gene therapy for a targeted wild type virus infection. The method comprises the following steps: a. developing an in vitro assembly assay for the targeted wild type virus; b. identifying a family of small molecule assembly effectors that affects the wild type virus assembly; c. identifying the assembly effectors' binding pocket on the targeted wild type viral structural protein by structural or chemical interaction methods; d making site directed mutagenesis to obtain at least one amino acid mutation so that the resultant protein structure has: the binding pocket filled up; and e. testing the mutant's self-assembly ability in the absence of viral assembly signal, or in the absence of the small molecule effectors, or that it has stronger association or faster kinetic assembly parameters.

In some embodiment of the method to identify dominant negative virus mutations, the targeted wild type virus is selected from HBV, Retroviridae (for example HIV), Flaviviridae (including HCV, Dengue Fever Virus, and West Nile Virus), Togaviridae (including WEE, VEE, Chikungunya, and Sindbis Virus), Herpesviridae (including Herpes Simplex 1, Herpes Simplex 2, Herpes Zoster (chicken pox and shingles), and Kaposi's Sarcoma Herpes Virus) and Papilomaviridae, such as HPV 16.

In some embodiment of the method to identify dominant negative virus mutations, the targeted virus is HBV, and the small molecule assembly effector is HAP or phenlypropenamide.

In one preferred embodiment, the dominant negative virus mutation for HBV core protein is located at the interface between subunits.

In one preferred embodiment, the method identified the dominant negative virus mutations on HBV core protein V124W.

In some embodiment of the method to identify dominant negative virus mutations, the targeted virus is HIV and the small molecule assembly effector is selected from the group consisting of PF-1385801, PF-3450074, and PF-3759857.

In one preferred embodiment, the method identified the dominant negative virus mutations on the HIV assembly effector binding site, which is located at the CA domain of HIV Gag protein.

This disclosure also provides a method for therapeutically treating a human being with chronic diseases implicated by a virus infection. The method comprising the following steps: a. genetically modifying at least one structural protein of said virus so that the resulting viral structural protein has aberrant assembly properties to abolish correct virion production; and b. delivering said genetically modified viral structural protein to said human being.

In some embodiment of the method to treat chronic virus diseases, the diseases are implicated by HBV or HIV infection.

This disclosure also provides a method to measure the expression level of a full length wild type HBV core protein and an artificially introduced dominant negative HBV core protein by building the dominant negative HBV core protein construct from a wild type HBV core protein truncated at residue 172 or 176. Due to the size difference the two can be separated by western blot and the levels be determined by mass spectometry, SDS-PAGE, or other arts.

These and other features, aspects and advantages of the present invention will become better understood with reference to the following figures, associated descriptions and claims.

TABLE 1

Southern blot analysis of WT, V124W
and co-transfection in Huh7 cells

|  | WT | V124W | WT:V124W = 1:1 |
|---|---|---|---|
| rcDNA | 100% (46%) | 3% (4%)* | 8% (7%)* |
| dlDNA | 100% (27%) | 6% (8%)* | 23% (15%) |
| ssDNA | 100% (19%) | 7% (5%)* | 37% (30%) |
| total DNA | 100% (19%) | 6% (3%)* | 31% (24%) |

Numbers in parenthesis are standard deviation.
*These values are at the limit of detection.

TABLE 2

Western blot analysis of WT, V124W
and co-transfection in Huh7 cells

|  | WT | V124W | WT:V124W = 1:1 |
|---|---|---|---|
| core protein | 100% (39%) | 60% (14%) | 66% (21%) |

Numbers in parenthesis are standard deviation.

Figure 10:
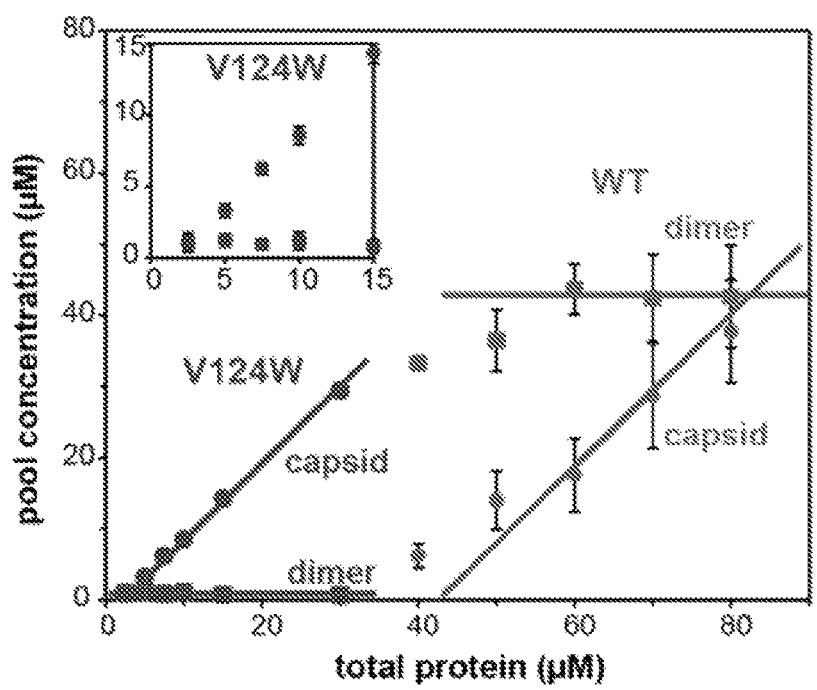

FIG. 10. V124W capsids were thermodynamically more stable than WT. V124W and WT dimers at different initial concentrations were induced to assemble by 100 mM NaCl and equilibrate for 72 h at 23° C. Capsid and dimer were separated by SEC and quantified in terms of dimer concentration in each pool. The pseudo-critical concentration was about 43 µM for WT and about 1 µM for V124W, a 40-fold difference. Each point was repeated 3 times for WT and 4 times for V124W.

TABLE 3

Thermodynamic parameters of HBV Cp149-WT
and V124W at 100 mM NaCl, 23° C.

|  | WT | V124W |
|---|---|---|
| $\Delta G_{contact}$ (kcal/mol) | −2.74 ± 0.04 | −3.84 ± 0.14 |
| $K_{D, apparent}$ (μM) | 43.28 ± 4.97 | 0.99 ± 0.42 |

Figure 11:
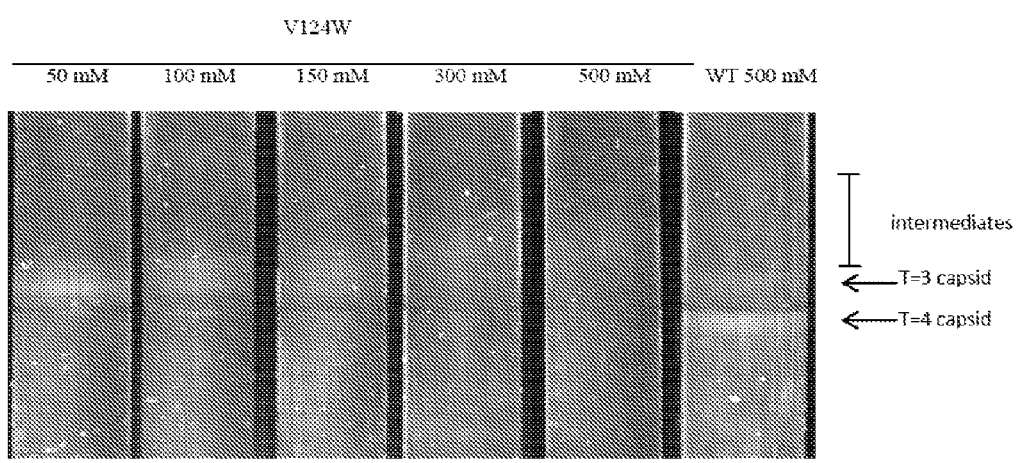

FIG. 11. A 10%-40% sucrose gradient separates Cp149-V124W assembled capsid and kinetically trapped intermediates. Wild type Cp149 assembles into both T=4 (lower band) and T=3 (upper band) capsids at 500 mM NaCl (far right). Cp149-V124W produces a high yield of T=3 capsid at 50 mM NaCl compared to wild type Cp149. With increasing the NaCl concentration, less capsids and more kinetically trapped intermediates were observed for Cp149-V124W assembly.

Figure 12:
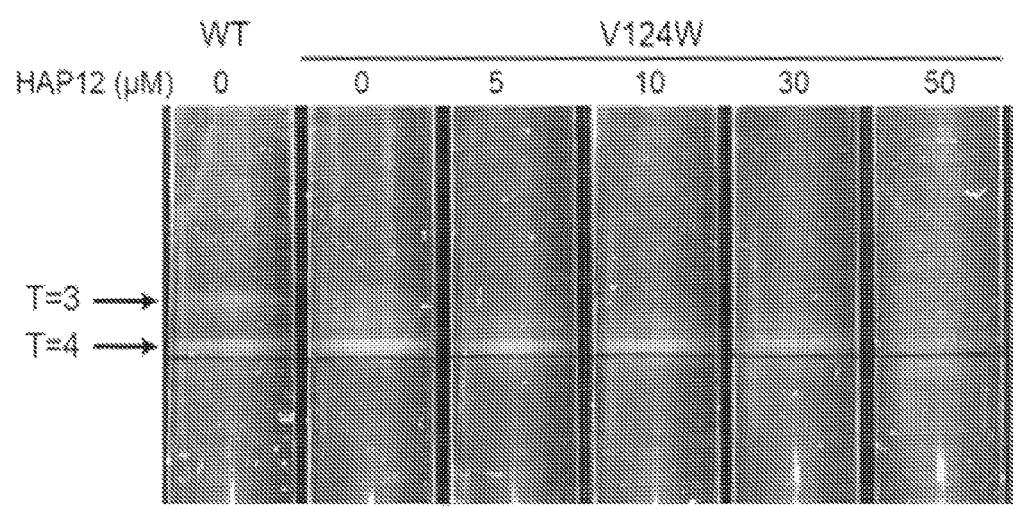

FIG. 12. A 10%-40% sucrose gradient centrifugation of V124W assembly products with HAP12. The arrows pointed the position of WT T=3 and T=4 capsids. Without HAP12, V124W mainly assembled into T=4 capsids. T=4 capsid band existed at low HAP12 concentration and decreased and disappeared at 50 μM HAP12.

Figure 13:
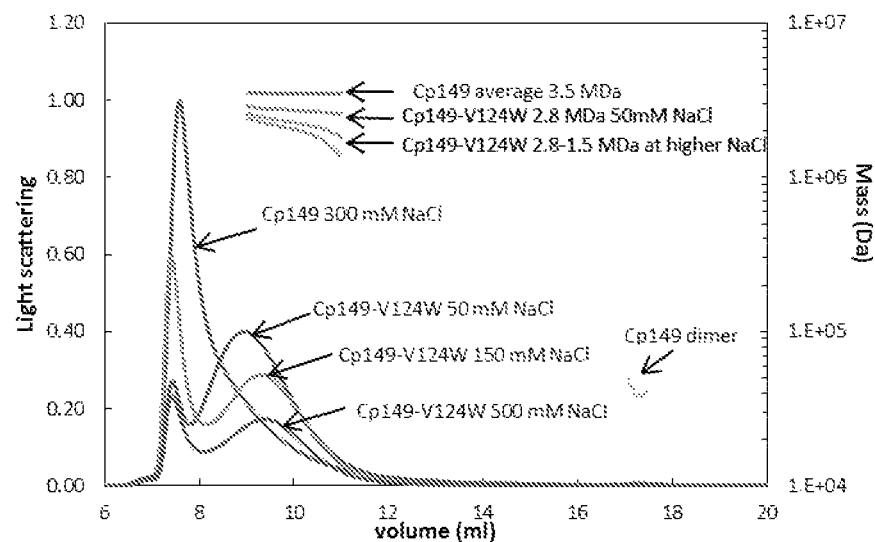
Figure 13:
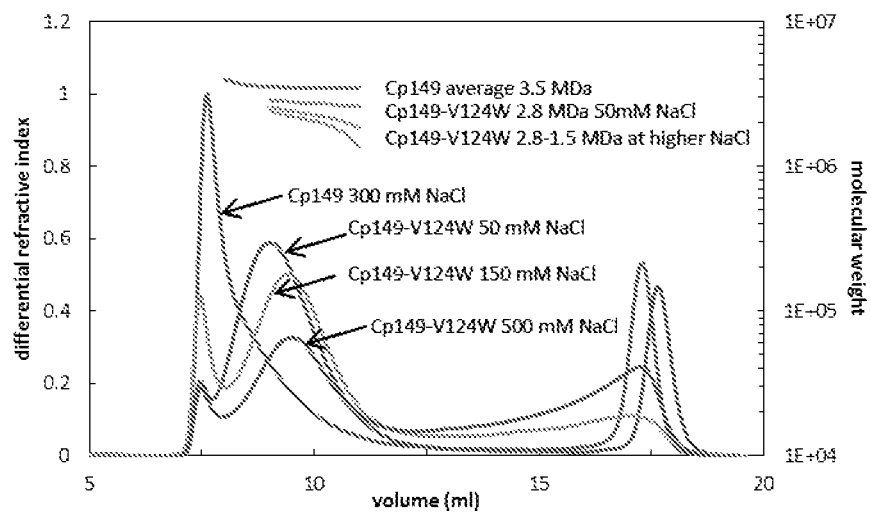

FIG. 13. Multi-angle laser light scattering demonstrates that the average molar weight of Cp149-V124W assembly product decreases with the increasing of ionic strength. Wild type Cp149 assembles into a mixture of T=4 (4 MDa) and T=3 (3 MDa) capsids, with an average molar weight 3.5 MDa. The average molar weight for Cp149-V124W assembly products ranges from 2.8 MDa (low NaCl) to a smear 2.8 MDa-1.5 MDa (high NaCl). The chromatography shows the differential refractive index of assembly products. The peak around 7.5 ml is due to large aggregations. The peak around 9 ml represents the capsid and intermediates peak, which shifts to larger volume with the increasing of ionic strength in Cp149-V124W assembly. The wild type Cp149 dimer elutes at 17.2 ml, which is earlier than the Cp149-V124W dimer. The different retention time of wild type Cp149 and Cp149-V124W dimer indicates a possible conformational difference. We also observed a peak which elutes earlier than the dimer in Cp149-V124W assembly with moderate to high NaCl. With the increasing concentration of NaCl, this peak becomes higher, implying the accumulation of kinetically trapped small assembly intermediates or nuclei.

Figure 14:
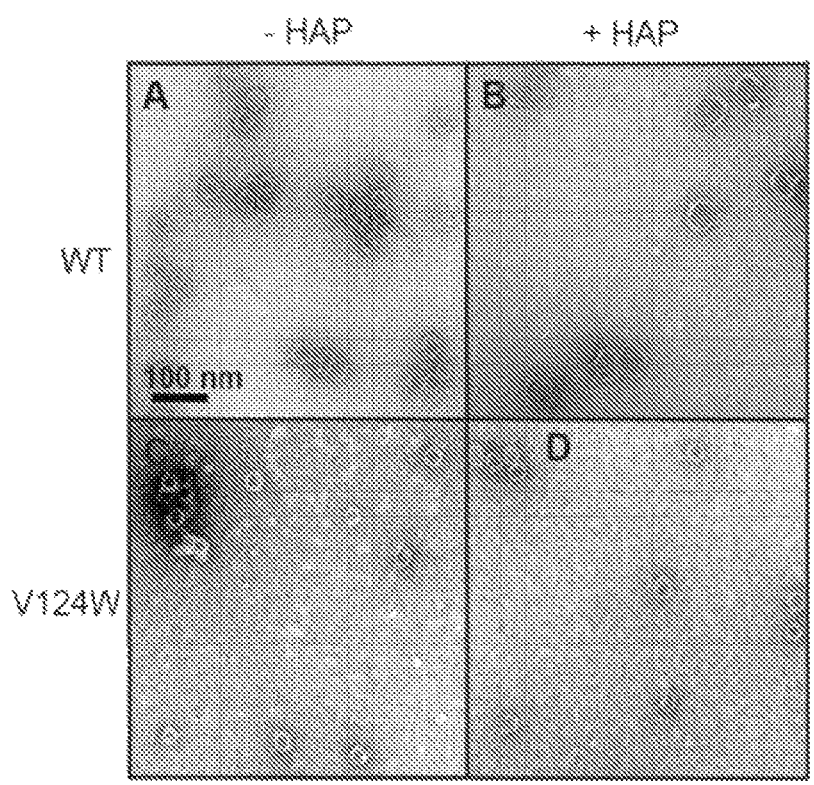

FIG. 14. Negative stained electron micrographs of WT and V124W assembly products. (A) 10 μM WT, 500 mM NaCl, no HAP12. (B) 10 μM WT, 50 mM NaCl, 20 μM HAP12. (C) 10 μM V124W, 50 mM NaCl, no HAP12. (D) 10 μM V124W, 50 μM NaCl, 20 μM HAP12. Figure A is a control showing the normal HBV WT capsids. HBV T=4 capsids are 35 nm in diameter. T=3 capsids are 31 nm in diameter. V124W assembled into capsid-like particles in the absence and presence of HAP12. WT assembled into aberrant structures in the presence of HAP12, which were much larger than normal capsids. The scale bar, representing 100 nm, applies to all images.

Figure 15:
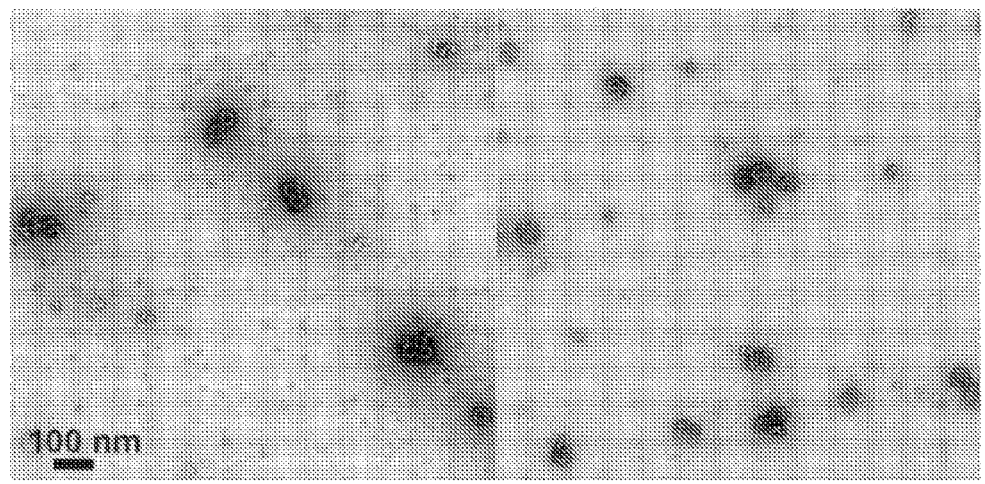

FIG. 15. Negatively stained electron micrographs of V124W assembly products with 60 μM HAP12. Capsid like particles and broken capsid structure were observed. No massive structure as seen in WT assembly with HAP12 (FIG. 14) were observed. Scale bar represents 100 nm.

Figure 16:
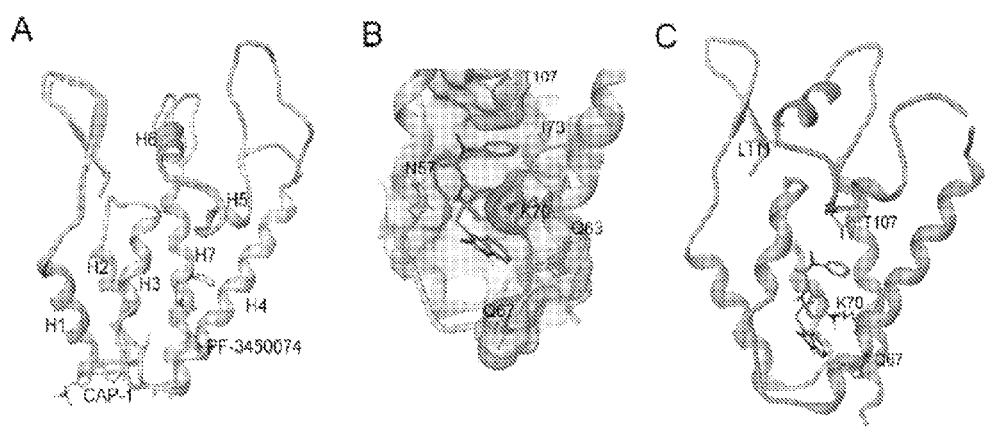

FIG. 16. Structure of the novel inhibitor binding site and context in the NTD of HIV CA protein. (A) overlays of capsid structures with PF-3450074 in blue and CAP-1 in pink bound to capsid N-terminal domain. (B) close up view of PF=3540074 site (binding site residues labeled in black, R1-3 sub-pockets labeled in purple). In the R1 sub-pocket PF-3450074 makes hydrophobic interactions with Ile-73, Aka-105, Thr-107, Tyr-130 and a stacking interaction with the side chain of Asn-53. The benzyl group R2 makes a number of hydrophobic interactions in a sub-pocket formed by the side chains of Met-66, Leu69, Va159, Ile-73 and Leu-56. The R3 sub-pocket is only partially occupied by the indle group, forming interactions with the side chains of Met-66, Gln-67, Lys-70 and Gln-63 amide. The indole NH forms a hydrogen bond interaction with the side chain amide of Gln-67 via a water molecule, while an Asn-57 forms a key hydrogen bond with the cis amide bond of PF-3450074. (C) location of resistant mutations (purple) in relation to PF 3450074 capsid binding site (PDB ID code 2XDE) (cited from PLos Pathogens, Volume 6, issue 12, e1001220).

Figure 17:
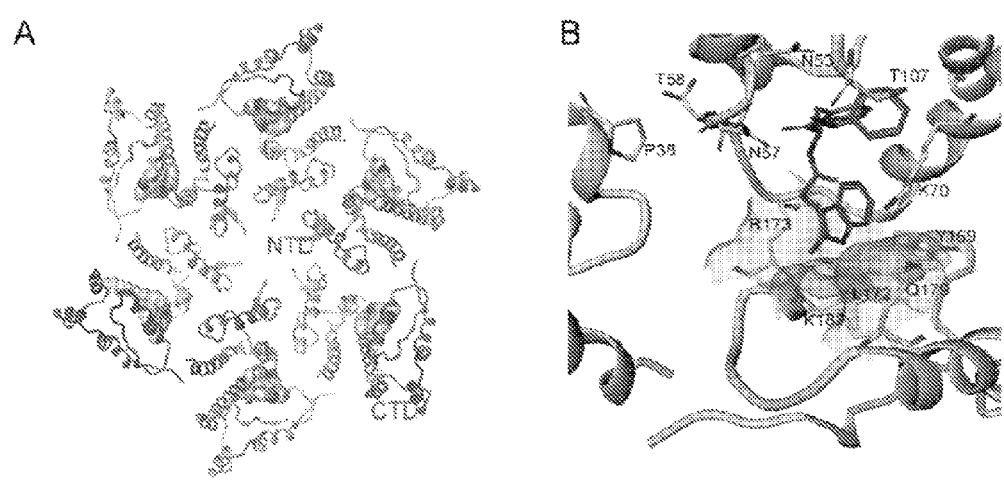

FIG. 17. Model of Inhibitor effects at the NTD-CTD interface of HIV CA. (A) a model of HIV capsid in hexameric complex with PF-3450074 bound in each of the binding pockets (each of the six full length CA monomers are colored differently. (B) close up view of model of interface between adjacent N terminal subunits (green and blue) and the C terminal domain of an adjacent monomer (pink) in assembled capsid. PF 3450074 highlighted in purple, Residues highlighted Pro 38 (adjacent N terminal domain green), Asn-53, Asn-57, Thr-58, Lys-70, Thr-107, (N-terminal domain blue), Tyr-169, Leu-172, Arg-173, Gln-179, Lys-182 (C-terminal domain pink). (cited from PLos Pathogens, Volume 6, issue 12, e1001220).

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected. For example, this disclosure uses one particular HBV strain as the illustrative embodiment. It should be kept in mind that HBV has multiple strains sharing conserved core protein sequences. Those manipulations that reflect the similar effect of the illustrative example are included in the scope of this disclosure.

Unless defined otherwise, the scientific and technology nomenclatures have the same meaning as commonly understood by a person in the ordinary skill in the art pertaining to this disclosure. Generally, the procedures for cell culture, infections, molecular biology methods and the like can be found in the art.

Antiviral drugs are a class of medication used specifically for treating viral infections. Like antibiotics for bacteria, specific antivirals are used for specific viruses.

Most of the antiviral drugs now available are designed to help deal with HIV, herpes viruses (best known for causing cold sores and genital herpes, but actually the cause of a wide range of other diseases, such as chicken pox), the hepatitis B and C viruses, which can cause liver cancer, and influenza A and B viruses. Researchers are working to extend the range of antivirals to other families of pathogens.

Designing safe and effective antiviral drugs is difficult, because viruses use the host's cells to replicate. This makes it difficult to find targets for the drug that would interfere with the virus without also harming the host organism's cells. Moreover, the major difficulty in developing vaccines and anti-viral drugs is due to viral variation.

Vaccines bolster the body's immune system to better attack viruses in the "complete particle" stage, outside of the organism's cells. Vaccines are very effective on stable viruses, but are of limited use in treating a patient who has already been infected. They are also difficult to successfully deploy against rapidly mutating viruses, such as influenza (the vaccine for which is updated every year) and HIV. Antiviral drugs are particularly useful in these cases.

The general idea behind modern antiviral drug design is to identify viral proteins, or parts of proteins, that can be disabled. These "targets" should generally be as unlike any proteins or parts of proteins in humans as possible, to reduce the likelihood of side effects. The targets should also be common across many strains of a virus, or even among different species of virus in the same family, so a single drug will have broad effectiveness. For example, a researcher might target a critical enzyme synthesized by the virus, but not the patient, that is common across strains, and see what can be done to interfere with its operation.

Once targets are identified, candidate drugs can be selected, either from drugs already known to have appropriate effects, or by actually designing the candidate at the molecular level with a computer-aided design program.

The emergence of antivirals is the product of a greatly expanded knowledge of the genetic and molecular function of organisms, allowing biomedical researchers to understand the structure and function of viruses, major advances in the techniques for finding new drugs, and the intense pressure placed on the medical profession to deal with the human immunodeficiency virus (HIV), the cause of the deadly acquired immunodeficiency syndrome (AIDS) pandemic, and many other chronic viral diseases that traditional vaccines or other means of viral treatments have their great limitations.

Researchers working on such "rational drug design" strategies for developing antivirals have tried to attack viruses at every stage of their life cycles. Viral life cycles vary in their precise details depending on the species of virus, but they all share a general pattern:

Attachment to a host cell.
Release of viral genes and possibly enzymes into the host cell.
Replication of viral components using host-cell machinery.
Assembly of viral components into complete viral particles.
Release of viral particles to infect new host cells.

The target proteins can be manufactured in the lab for testing with candidate treatments by inserting the gene that synthesizes the target protein into bacteria or other kinds of cells. The cells are then cultured for mass production of the protein, which can then be exposed to various treatment candidates and evaluated with "rapid screening" technologies.

Viruses such as hepatitis B, hepatitis C, and Human Immunodeficiency Virus are among many pathogens causing chronic infections in large population around the world. These infections pose great health risk for the patients. Treatment for these viruses are targeted to their specific life cycle, mostly tailored to disrupt virus genome synthesis.

Hepatitis B virus (HBV) is an enveloped virus with an icosahedral core. The core is assembled in the cytoplasm from core (capsid) protein, viral pregenomic RNA, viral reverse transcriptase, and a few host proteins. For HBV, the core plays indispensable roles in viral DNA synthesis from the pregenome and intracellular trafficking. The predominant antiviral strategy is to attack a viral enzyme, usually the viral DNA or RNA polymerase. In HBV this enzyme is a reverse transcriptase. For example, HBV is routinely treated with reverse transcriptase inhibitors such as LAMIVUDINE®, ADEFOVIR®, ENTECAVIR®, and TENOFOVIR®. However, the reverse transcriptase inhibitors each have issues including side effects, generation of resistance, and cross reactivity with HIV therapies. Plus these drugs cannot be used without some risk of a potentially fatal viral rebound should treatment be halted. Resistance can have broader consequences because of the extensive gene overlap in HBV, since some reverse transcriptase mutations lead to surface protein that is insensitive to antibodies generated by the HBV vaccine.

An alternative strategy is to target the assembly of the virus capsid with assembly effectors. By altering virus assembly kinetics, these antiviral drugs halt virus development successfully, either causing incorrect packaging or abortion of packaging. Both chemicals and modified viral structural protein are contemplated in this disclosure to achieve antiviral effect through targeting viral assembly.

Figure 1:
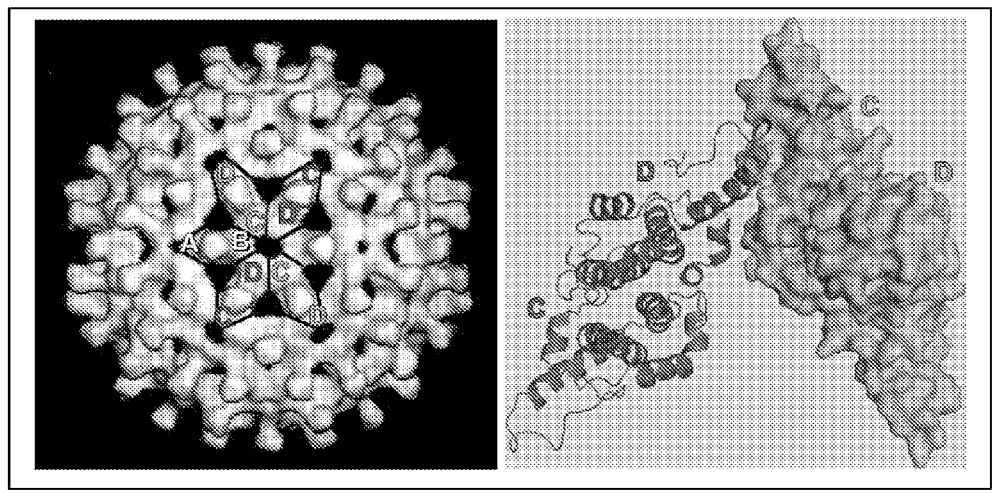
FIG. 1. HBV capsid and the antiviral drug HAP binding site. The HBV capsid is a T=4 complex of 240 proteins (120 dimers) where the core protein is in four quasi-equivalent environments, referred to as A, B, C, and D (FIG. 1, left). In the crystal structure with bound HAP, the HAP antiviral was only found in the C subunit at the C-D interface (FIG. 1, right). In the figure, bound HAP is a space-filing model (yellow), the C subunit shows a surface shaded (green) and the incoming D subunit is a ribbon diagram (purple).

Take the example of the HBV capsid, the protein shell of the virus core is an icosahedral complex comprised of 120 core protein dimers (Cp), where the monomers fit into four similar but distinct environments, A, B, C, and D (FIG. 1). Correct assembly of the capsid is critical for packaging the RNA form of the viral genome and the reverse transcriptase, correct reverse transcription of the RNA to the DNA of the infectious virus, and intracellular trafficking of the virus and virus morphogenesis and egress. Cp may also play a role in maintaining the viral genome in chronically infected cells.

Virus assembly is a process involving packaging the viral genomic material and building a protective capsid shell. Capsid assembly begins with a rate limiting 'nucleation' step followed by addition of subunits, generally one at a time. Altering intracellular Cp activity drastically interferes with infection. Heteraryldihydropyrimidines (HAPs), first identified by scientists at Bayer AG as having anti-HBV activity in a cell culture-based screen, act in a capsid protein-specific manner. HAPs accelerated HBV assembly, stabilized Cp-Cp interactions, and subtly altered local Cp-Cp interaction geometry leading to grossly aberrant structures. Therefore, HAPs have been suggested as potential antiviral therapy. However, relatively high HAP concentrations were necessary to alter geometry of HBV capsid and the antiviral effect is fundamentally kinetic. To effectively achieve the inhibition of virus assembly, a high concentration of antiviral small molecules are in need, prompting expensive but necessary efficacy and safety test on these small molecules before it can be used in any virus infection treatment. At this time, HAPs and any other small molecules that affect virus assembly are still experimental drugs. They have not been used in humans. We note that HAPs have been suggested as a replacement for Rerverse Transcriptase inhibitors or as a supplement to them in a multivalent therapy.

Another well studied virus is retrovirus exemplified by Human Immunodeficiency Virus (HIV). Retroviruses have two structural genes, gag and env. The gag gene provides the basic physical infrastructure of the virus whereas env encodes the surface glycoprotein complex. gag (group-specific antigen) codes for the Gag polyprotein, which is processed during maturation to MA (matrix protein, p17), CA (capsid protein, p24), SP1 (spacer peptide 1, p2); NC (nucleocapsid protein, p7), SP2 (spacer peptide 2, p1) and p6.

The capsid protein (CA) of HIV-1 plays critical roles in both late and early stages of the viral replication cycle and is viewed as an important unexploited therapeutic target. At the earliest stages of particle assembly, the interactions between CA domains of the Gag polyprotein help drive the formation of immature particles at the membrane of host cells. Gag is associated to the membrane by MA and specifically to viral RNA by NC. After the release of immature particles from infected cells, proteolytic processing of the Gag polyprotein is completed, leading to reorganization of domains so that CA forms the conical complex common to mature HIV. Defects in the stability of CA-CA interactions lead to defects in virion formation. After virus fusion with a target cell, the core is released into the cytoplasm and CA is thought to undergo a controlled disassembly reaction in order for reverse transcription of the viral genome to occur properly.

A recent publication (Blair et al (2010) PLoS Path 6, e1001220) shows that small molecules (e.g. PF3450074) can bind to the N-terminal half of the CA domain and stimulate assembly resulting in a concomitant decrease in production of HIV virions. This mechanism of action is thus analogous to that of the HAPs. Similarly the PF3450074 pocket can analogously be filled to produce an assembly hyperactive molecule.

This disclosure provides material and method of dominant negative viral capsid protein mutations to altogether eliminate the need for long term therapy with antivirals, such as HAPs or its homologs to treat HBV. Similarly, we explain how assembly effectors can be used to generate dominant negative mutants to HIV. Thus, we developed a single treatment to accomplish long term gene therapy for many chronic virus infections and related chronic diseases.

Figure 9:
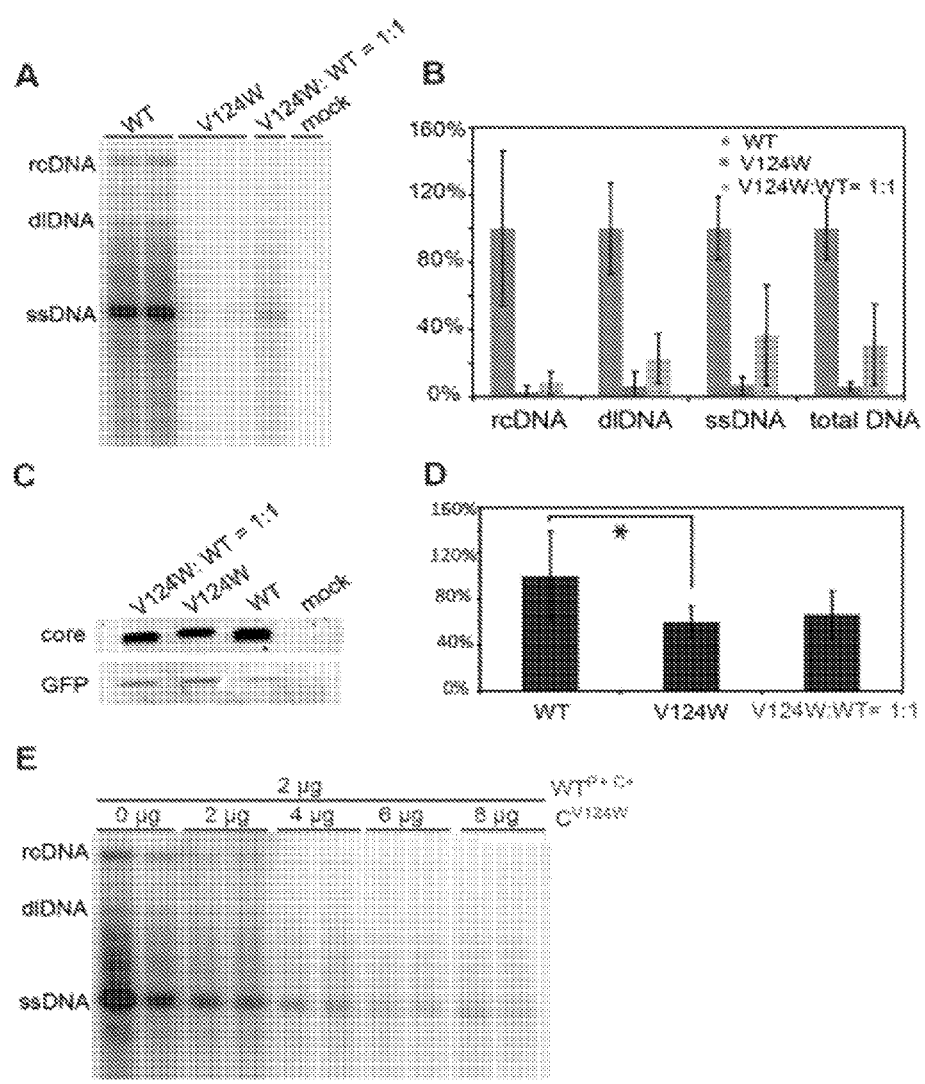
FIG. 9. V124W had a dominant negative effect on HBV replication in cell culture. (A) A Southern blot showed that V124W expression profoundly suppressed viral DNA synthesis. WT and V124W lanes were shown in duplicates. Mock transfection did not express any HBV proteins. (B) Quantification of Southern blot data from three independent transfections. WT yields of rcDNA, dlDNA, ssDNA and total DNA were normalized to 100%. Yields of DNA in transfections with V124W, exclusively, were 3-7% of WT. Co-transfections of WT and V124W yielded 8-37% of the DNA in WT pools (Table 1). (C) A western blot of core protein level in WT, V124W and co-transfection experiments. (D) Quantification of western blot data from three independent transfections. V124W core protein yield was statistically less than WT (indicated by the star). However, there was no statistical difference between the core protein levels in 1:1 co-transfection and WT transfection alone (Table 2). (E) V124W titration of WT expression in Huh7 cells. With increasing V124W core protein expression, WT DNA synthesis was suppressed.

Overall based on general design principles, we present a genetically modified viral structural protein for therapeutically inhibiting virus biosynthesis. This designed, genetically modified structural protein enhances self-assembly and co-assemble with wildtype virus structural protein at an inappropriate time or place, resulting in inhibition of virus production. This assembly-enhancing effect results in a dominant negative phenotype (see FIG. 9, mutant suppressing wildtype viral genome expression in the co-transfection experiment), i.e., it will overwrite wildtype virus or any other assembly effector binding site mutants' assembly kinetics, leading to incompetent virion packaging.

Assembly studied by means of biochemical and structural analyses indicates that in the absence of the correct viral assembly signal, these dominant negative capsid proteins initiate and support viral assembly and co-assembly with wildtype viral core proteins, with the result of inhibiting further viral replication. The accelerated assembly or co-assembly by the dominant negative mutant is largely independent from assembly effectors, rendering the wildtype virus insensitive to assembly effectors. This technology eliminates the need of using antiviral compound to treat certain named chronic viral diseases as the prematurely assembled complexes are incapable of reproduction of competent viruses, the chronic viral diseases, for example, those caused by HBV, HIV, HCV, Dengue Fever Virus, West Nile Virus, viruses in Togaviridae, including WEE, VEE, and Herpesviridae including herpes simplex 1, herpes simplex 2, herpes Zoster (chicken pox and shingles), Kaposi's sarcoma virus, and Papillomaviridae including HPV 16, are contemplated in the therapy scope under this strategy disclosed in this invention.

HBV Dominant Negative Mutant Identification

We designed and tested a HBV core protein mutant (SEQ. ID. NO:1 Cpdominant1) and confirmed the HBV's core protein HAP binding site at the core protein interface, solved by low-resolution crystallography.

Figure 2:
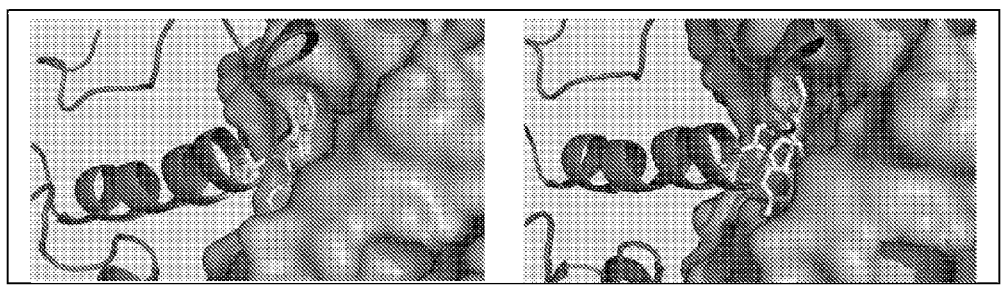
FIG. 2. A close-up of the HAP binding site on HBV capsid and HBV Cpdominant1. The HAP sits in a depression in the C subunit. The site is capped by the D subunit. Valine 124 of D (FIG. 2, left panel), shown as a white stick model, is part of that cap and abuts the HAP molecule (yellow stick model). When mutated to a tryptophan, V124W, also in white, (FIG. 2 right panel) the mutant amino acid overlaps the HAP site.

FIG. 2 shows a close-up of the HAP binding site on HBV capsid and the HBV Cpdominant1 mutant. The HAP sits in a depression in the C subunit. The site is capped by the D subunit. Valine 124 of D (FIG. 2, left panel), shown as a white stick model, is part of that cap and abuts the HAP molecule (yellow stick model). When mutated to a tryptophan, V124W, also in white, (FIG. 2 right panel) overlaps the HAP site.

Figure 3:
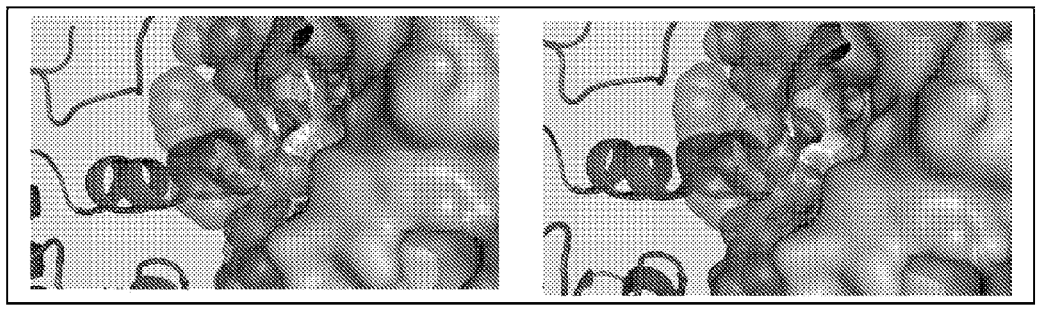
FIG. 3. HAP site filled in HBV Cpdominant1. Viewed as a space-filling surface contour, the valine at position 124 of the wild type protein clearly leaves a gap in wild type structure. The V124W mutation overlaps the HAP position and fills that gap (FIG. 3). By filling the gap, V124W induces a stronger protein-protein interaction and also, apparently, stabilizes the assembly-active form of core protein to speed up assembly. The V124W phenotype is identical to the effects of HAP on virus assembly in vitro and in vivo.
Figure 4:
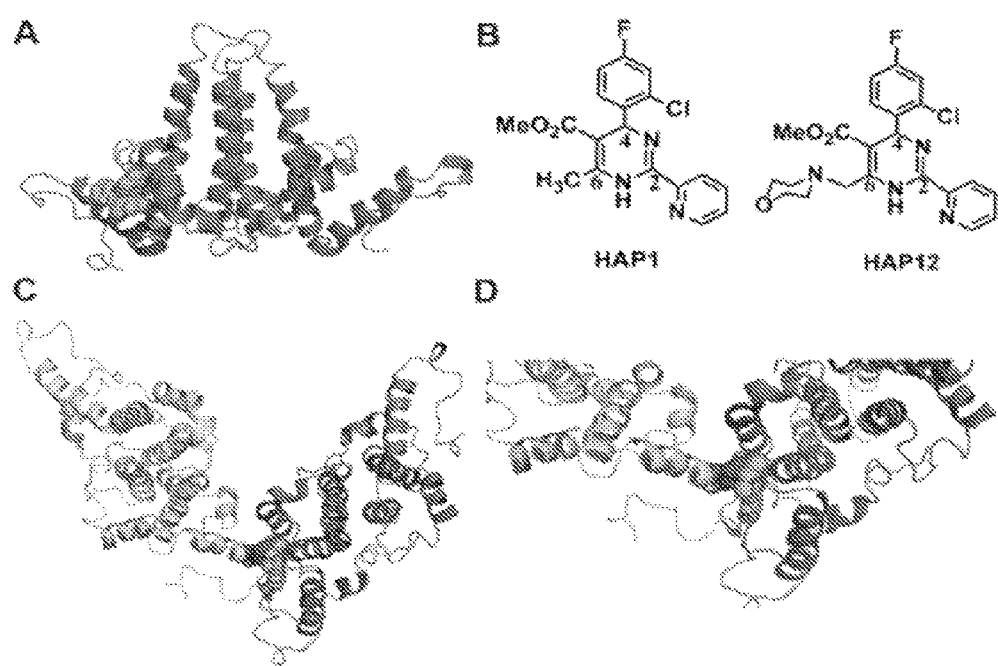
FIG. 4. A Model of Cp149-V124W dimer structure shows that V124W overlaps the HAP binding site. (A) A side view of the HBV Cp149-WT ribbon structure with HAP1 (cyan spheres) bound (PDB: 2G34). (B) The structure of HAP1 and HAP12. HAP12 has an additional six-member ring linked to the methyl group at position 6. (C) A model of Cp149-V124W was generated based on Cp149 (PDB: 2G34) with the program Coot by changing the V124 of core protein D monomer into a W; the rotamer in this model accounts for 32% of W rotamers observed in high resolution structures. Viewed from the capsid interior, the HAP1 binding site is seen at the dimer-dimer interface. The V124W mutation (red spheres) overlaps HAP1 and partially fills the HAP binding site. The two dimers forming the site are colored yellow and magenta. (D) A close-up view of the HAP binding site at the V124W dimer-dimer interface.
Figure 5:
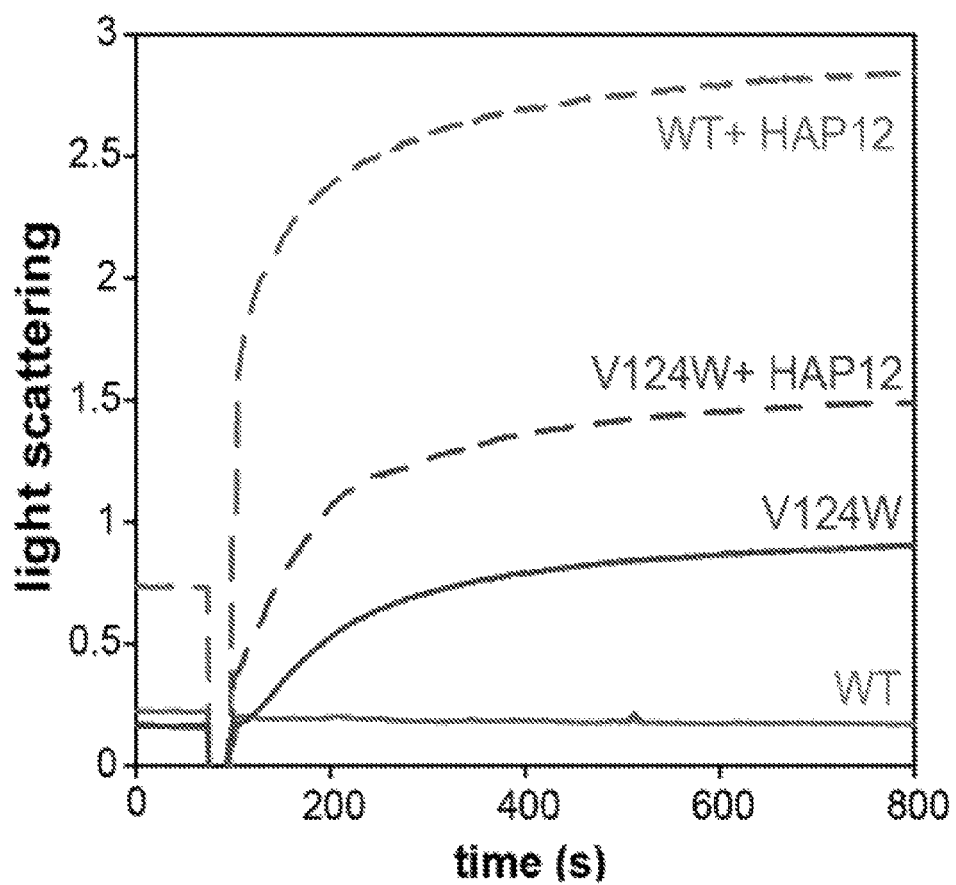
FIG. 5. V124W assembly kinetics were faster than WT and resistant to HAP. 10 µM protein (WT or V124W) incubated with or without 20 µM HAP12 was induced to assemble by 50 mM NaCl and the first 800 seconds of assembly kinetics were monitored by 90° light scattering. Under these conditions, WT did not assemble without HAP12. HAP12 profoundly sped up WT assembly. V124W assembled rapidly under these same conditions, but HAP12 only increased V124W assembly kinetics by twofold. Each light scattering trace was an average of three to four independent experimental results.

FIG. 3 shows HAP site filled by HBV Cpdominant1. Viewed as a space-filling surface contour, position 124 clearly leaves a gap in wild type structure. The V124W mutation overlaps the HAP position and fills that gap (FIG. 3 and FIG. 4). By filling the gap, V124W induces a stronger protein-protein interaction and also, apparently, stabilizes the assembly-active form of core protein to speed up assembly. The V124W phenotype is identical to the effects of HAP on virus assembly in vitro and in vivo.

The HBV capsid is a homopolymer of the core protein. Residues forming the HAP site are: from the C subunit: F24, P25, L30, T33, W102, I105, S106, F110, Y118, I139, and L140; from the 'D' subunit: V124, R127, T128.

The following chart shows the result of identification of key amino acid in HBV core protein that demonstrates interaction with HAP and affect HAP induced self-assembly.
Demonstrated Assembly Activating Mutations
V124X, where X=W, F
Predicted Assembly Activating Mutations
V124X, where X=Y, L, I
T128X, where X=W, F, Y
I139X, where X=W, F, Y, M
L140X, where X=W, F, Y, M
Y118X, where X=W
F110X, where X=W
S106X, where X=W, F, Y, M, L
I105X, where X=W, F, Y, M
T33X, where X=W, F, Y, M
L30X, where X=W, F, Y, M
P25X, where X=W, Y, F, L This finding suggests the important role of core protein interface in regulating capsid assembly. Similar designs to other viral capsid protein mutation that will bring the mutant protein to a conformation that displays constitutive active assembly effector bound status is comtemplated. Such design will fulfill the purpose of producing dominant negative assembly effector bound viral core protein for each identified virus.

HBV Cpdominant1 Alters Viral Assembly Kinetics and it is HAP Resistant

Kinetic studies revealed that the mutant HBV Cpdominant1 mimicked HAP behavior, acting as a de facto HAP-bound HBV core protein: the mutant HBV Cpdominant1 assembled faster and further than wild type core protein, and dominantly interfered with viral replication. Co-assembly with wildtype HBV core protein was observed and the kinetics of wildtype virus core protein assembly is altered by the presence of these HAP-insensitive Cpdominant1.

By using the HAP-like behavior of this mutant, we are able to study the mechanism of HAPs on virus replication in cell culture, which in turn helps us understand the action of assembly effector better and design more effective assembly effectors.

Furthermore, this HAP-resistant mutant showed that emergence of viral resistance to assembly effectors through mutation at the binding site could be detrimental to the virus, suggesting that assembly effectors, or mutations making constitutive assembly active structural protein would be a new powerful antiviral therapy for virus infection.

Figure 6:
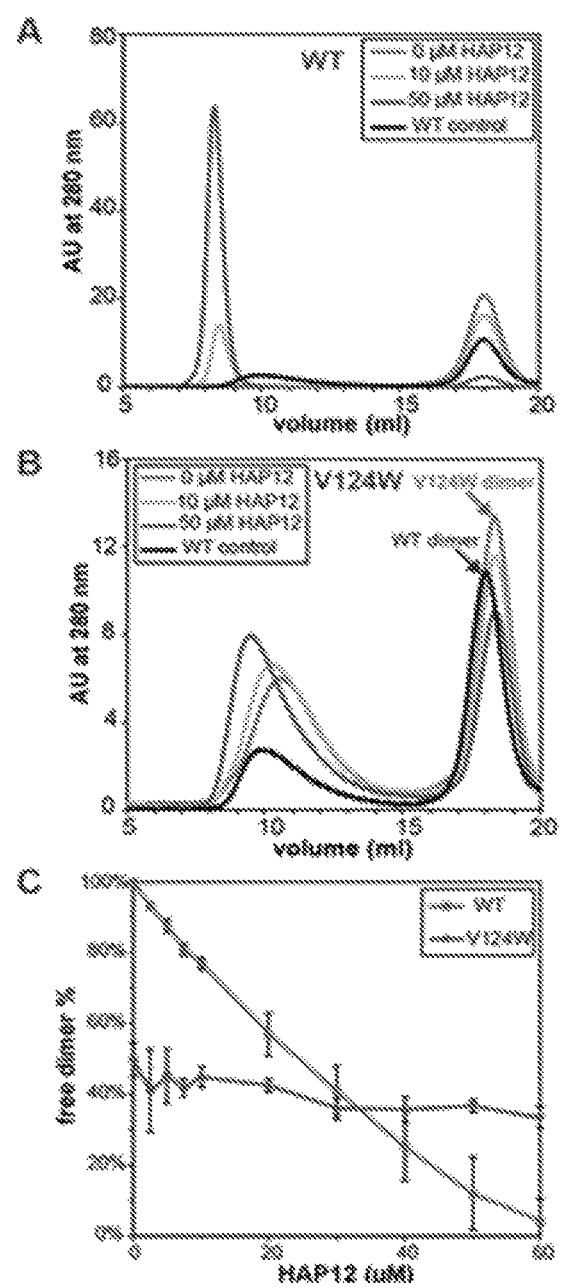
FIG. 6. Effect of HAP12 on V124W and WT assembly. (A) Representative chromatograms of 10 µM WT assembly with HAP12. A standard chromatogram of 10 µM WT assembly at 300 mM NaCl without HAP12 is shown in black line in both (A) and (B) to indicate the WT capsid and dimer positions. The void volume ($V_0$) for the 21 ml Superose 6 column is 7 ml. WT capsid eluted at 10 ml; WT dimer eluted at 18 ml; small molecules, including HAP12 and β-mercaptoethanol eluted after 20 ml. With increasing HAP12, the WT dimer peak decreased and an assembled dimer peak appeared, increased in peak area, and shifted progressively to the void volume. (B) Representative chromatograms of 10 µM V124W assembly with HAP12. With increasing HAP12, the V124W capsid peak eluted earlier, but not into the void volume, unlike WT. V124W dimer eluted later than WT dimer. (C) HAP12 titration on WT and V124W assembly. WT assembly was enhanced from no assembly without HAP12 to 95% assembly with 60 µM HAP12. The extent of V124W assembly was only changed from 50% to 35% at 60 µM HAP12.

Taking HBV core protein as an example, our study indicates the dominant negative mutant of viral capsid protein is a de facto antiviral assembly effector bound protein, and it demonstrates noncompetitive nature to the corresponding assembly effector HAPs, i.e. the dominant negative mutants are insensitive to further presence of antiviral compounds (see FIG. 6, HAP only slightly increases V124W dimer's assembly rate). The introduction of these dominant negative viral capsid proteins into a wild type virus-infected living system predominantly alters the kinetics of other corresponding viral capsid protein assembly. The net effect, therefore, is that these dominant negative mutants overwhelm viruses' escape strategy, rendering itself insensitive to antiviral compounds. This dominant negative activity will eliminate the need for antiviral compounds and the side effects they may bring to the living system.

This technology is appropriate for gene therapy for chronic viral diseases, in particular using a vector that is targeted toward an appropriate organ. An example is the use of hepatotropic Adeno-Associated Virus for dominant negative HBV core protein expression. The targeted expression of dominant negative HBV core protein alters the kinetics and thermadynamics of wild type core proteins' assembly and disrupt any effective virion packaging.

As an example, this disclosure uses HBV capsid to illustrate how to use mutant capsid protein to change the kinetic of virus assembly, therefore acts as constitutively active viral assembly machinery in the absence of proper viral genome encapsidation. The end result is that the mutant capsid either self-assemble or co-assemble with wild type capsid protein in the absence of viral nucleic acid, therefore producing empty virions without proper genome material inside.

In the case of mutant HBV capsid, the invention in its full realization consists of a stable DNA episome, inserted into the nucleus of infected hepatocytes that carries an open reading frame encoding a mutant HBV core protein as set forth in SEQ. ID. NO: 40 (Cpdominant1) under the control of a relatively strong promoter. The Cpdominant1 is a core protein that has enhanced assembly properties, based on a mutationally-filled HAP pocket. Cpdominant1 nucleates capsid assembly independent of the normal signals for assembly, acting like a constitutively HAP-poisoned Cp. Like any assembly effector-treated cell, the effect is to quickly deplete the wild type Cp dimer by producing defective Cp complexes and preventing formation of wild type cores and hence infectious virions.

The mutation of Cp to fill the HAP pocket results in a protein that has aggressive HAP-like assembly behavior. HAPs are able to speed up assembly by as much as 5000-fold and decrease the threshold concentration of assembly by as much as 500-fold. The HAP binding site is a pocket at the Cp-Cp interdimer contact surface, between the C and D chains. The site is bounded by nine amino acids from the C subunit (L30, T33, W102, I105, S106, F110, Y118, I139, and L140), forming an invagination, and three amino acids from the D subunit (V124, R127, and T128), forming the cover. Notably, V124 makes more contacts with the HAP molecule than any other amino acid. The side chain of the point mutation V124W partially fills the HAP site, conferring HAP-like activity and also HAP insensitivity. This protein has a dominant negative phenotype and is thus named Cpdominant1.

When mixed with wild type Cp, Cpdominant1 induces assembly of non-viral polymers in the same way that HAP does, i.e. there is non-productive assembly. This altered assembly feature of the dominant negative core protein mutant further inhibits HBV virus mutation to escape binding of assembly effectors such as HAP. As such, Cpdominant1 and other similar concept HBV core protein mutations contemplated in the Examples create a de facto HAP-ligated core protein; such de facto HAP-ligated core protein predominantly engages wildtype and mutant HBV core proteins to produce defective viral particles, making HAP and analogous compounds irrelevant to antiviral therapy. Therefore, Cpdominant1 (and other similarly concepted core protein mutations that render dominant negative HBV core protein assembly) is HAP resistant, eliminating the need of HAP presence, but still demonstrating HAP effect.

In addition, downstream effects are also shown for Cpdominant1. Electronic microscopy studies and size exclusion column elution of co-assembled capsids indicates that morphologically normal particles that incorporated Cpdominant1 are formed at equilibrium. The mutant and coassembled are substantially more stable than wild type capsids. The increased stability appears to interfere with reverse transcription. The increased stability also interferes with capsid breathing, which appears to be involved in intracellular trafficking of capsids. The increased stability also will interfere with release of the viral genome to the nucleus.

Figure 8:
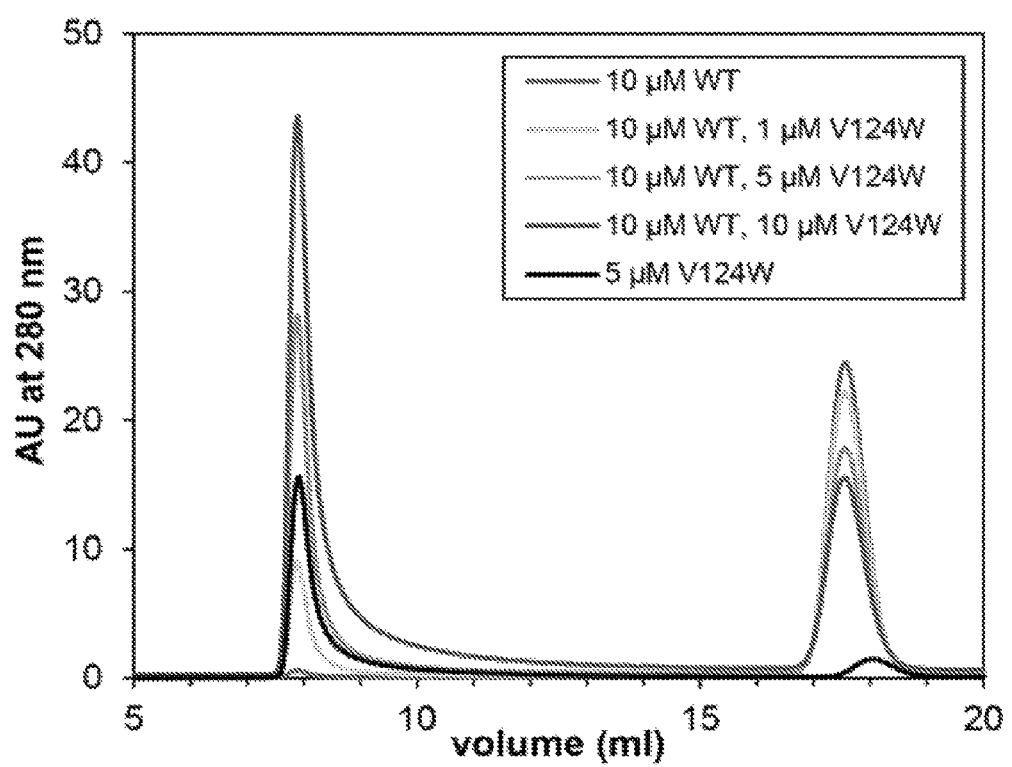
FIG. 8. Chromatograms showed that in co-assembly reactions, there was no detectable free V124W dimer at equilibrium. Representative chromatograms of 10 µM WT co-assembled with different concentrations of V124W. On this Superose 6 column, V124W dimer eluted at 18 ml and WT dimer eluted at 17.5 ml. In co-assembly elution profiles, dimer peak eluted at 17.5 ml, indicating no free V124W dimer at equilibrium.

Co-assembly studies also revealed that Cpdominant1 reduced wildtype capsid's threshold assembly concentration (see FIG. 8, with increased concentration Cpdominant1, wild type capsid at low concentration started to assemble and appear in Superose elution peak). This will translate into premature assembly in a living system infected with wild type virus, causing assembly without packaging viral RNA. Finally, because Cpdominant1 affects the threshold concentration of protein available for assembly, and free Cp dimer plays a role in stabilizing the HBV genome in the nucleus, prolonged exposure of a patient to Cpdominiant1 has the possibility of curing chronic infection.

Another example to modify capsid protein assembly kinetics is found by studying a group of assembly effectors that bind to HIV Gag protein's CA or SP1 domain. It is established that many mutations in these domains lead to defects in assembly (Forshey et al (2002) J Virol 76, 5667-5677; Datta et al (2011) J Virol 85, 4111-4121).

A series of HIV-specific assembly effectors have been described, PF-1385801, PF-3450074 and PF-3759857 that inhibit HIV replication. These molecules specifically target HIV-1 CA and, in infected cells, interfere with both the viral uncoating process and the formation of infectious particles. These molecules affect the morphology of nascent HIV particles by affecting CA structure and CA-CA interactions; in biochemical experiments they induce assembly indicating they activate nucleation and stabilize CA-CA contacts. High resolution co-crystal structures have been determined and illustrate a novel binding pocket in the N-terminal domain (NTD) of HIV-1 CA. Targeting this new binding pocket with small molecules results in broad-spectrum antiviral activity. A full description of these compounds effect on HIV CA protein is found in the following article: *HIV Capsid is a Tractable Target for Small Molecule Therapeutic Intervention*, Blair et al., *PLoS Pathogens* December 2010.

Briefly, PF1385801 and its several analogs demonstrated activity in antiviral assays using the MT-2 T cell line and HIV-1 NL4-3. The crystal structure of HIV-1 CA N terminal domain (NTD) protein in complex with PF3450074 was determined by using a CA protein construct that contained a single glycine residue in place of the cyclophilin binding loop (residues 87-99). PF3450074 occupies a preformed pocket in the HIV-1 CA NTD bounded by helices 3,4,5 and 7 (FIG. 16A). The R1 and R2 aromatic moieties of the compound occupy two hydrophobic subpockets and provide most of the key interactions which anchor the compound to the NTD (FIG. 16B). The indole substituent protrudes from the NTD R3 sub-pocket close to Lys 70.

In the evaluation of this novel series of antiviral compounds, an in vitro CA multimerization assay was conducted. Such assays can be used to measure the effect of compounds on the rate of formation of higher order CA multimers or tubes that are widely thought to represent many aspects of native core structure. PF 3450074 resulted in a significant increase in the rate of CA mutimeration. In the contrast, a structural analogue with no antiviral actgivity PF4159193 did not affect the kinetics of CA mutimerization, indicating that this profound effect on assembly was correlated with antiviral activity. Other antivirals specific to assembly, including CAP-1 and CAI, only inhibit late stage viral replication.

The binding site for PF-3450074 is distinct from the sites targeted by other antivirals such as CAP-1 CAI, and NYAD-1. PF-3450074 directly binds HIV CA. Mutations on CA that interfere with PF3450074's binding pocket renders HIV-1 virus resistant to PF3450074. It is likely the resistant mutant of 1-HIV-1 CA protein mimics the pharmacologic effects of these compounds, just like HBV V124W mimics HAPs. HIV capsid mutations proximal to the PF-3450074 binding pocket either destabilize or enhance the stability of viral cores and result in core-related defects in virus replication. Therefore, such mutations and the compounds described herein have analogous effects on inter-subunit capsid interactions.

A model of an assembled capsid hexamer in complex with PF-3450074 is shown in FIG. 17A, based on superpositioning of assembled capsid structures with the structure of the PF-3450074/CA complex. In the model, the R3 indole group which protrudes from the NTD in the structure localizes to the interface between capsid monomers in an assembled capsid and sits directly between the NTD of one capsid monomer and the C-terminal domain of another, making contacts to Tyr-169, Leu-172, Arg-173, Gln-179, and Lys-182 (FIG. 17B). This suggests the R3 indole group of PF3450074 could play a critical role in modulating inter-subunit interactions. Both the CA NTD contact residues described by the co-crystal structure and these putative C-terminal contacts are well conserved across viral strains, which is consistent with the broad spectrum antiviral activity observed for this series.

Thus, based on a published crystal structure of the CA-drug complex (PDB accession number 2XDE), the drug's binding site is a well conserved pocket lined with the following amino acids: Asn-53, Leu-56, Asn-57, Leu-69, Lys-70, Ile-73, Ala-105, and Thr-107 (FIGS. 16 and 17). From superposition of this structure over an equivalent NTD m the CA hexamer structure (PDB file 3H4E) we observe that the binding pocket is capped by Glu-35, Pro-38, Ser-178, Gln-179, Glu-180, Val-181, and Lys-182 from the neighboring CA (the numbering of residues is as in 3H4E). Our results with HBV indicate that mutating any of these residues to a tryptophan will partially fill the binding pocket probably resulting in an assembly hyperactive effect with a dominant negative result.

The study of HIV antiviral compounds described herein identified a new binding site on HIV-1 CA that can be targeted by a group of small molecule inhibitors. These small molecules inhibit the virus at two points in the replication cycle, both of which are related to assembly and capsid stability. It is unclear whether PF3450074 is specific in action to interactions of mature CA or also affect interactions between immature Gag polyproteins. PF 3450074 does not inhibit Gag association in HIV-1 transfected cells but phenylpropenamides do not prevent formation of normal looking HBV capsids. As PF3450074's site is highly conserved, it is feasible to develop dominant negative HIV-1 CA mutants that have broad spectrum antiviral effects. Specifically, administering HIV-1 CA dominant negative mutants that mimic the behavior of PF3450074 assembly effectors on HIV-1 CA protein can lead to defective HIV-1 particles.

In the following examples we have shown using herein disclosed strategy to identify salient sites of virus capsid protein assembly interface. These sites are mutated into assembly dominant negative phenotype which is resistant to assembly effectors and applied to chronic virus infected animal models to exert single treatment of gene therapy, eliminating the use of antiviral compounds in these chronic viral diseases.

EXAMPLES

Example 1. Assembly Effector-Based Design of Hepatitis B Virus Core Protein Mutant that Dominantly Interferes with Virus Replication In this example, based on a 5 Å structure of an HBV capsid co-crystallized with HAP1, we designed a core protein mutant that mimic the activity of HAPs. We confirmed the putative HAP binding site and proved that filling the HAP binding site confers HAP-resistance. The mechanism of HAP activity is proposed in the study as well. We mutated core protein residue 124 from V to W, which structurally filled the HAP site and increased the buried hydrophobic surface. V124W core protein showed enhanced assembly kinetics, strong association energy, HAP-resistance, and dominantly interfered with WT DNA synthesis in cell culture.

Materials and Methods

Cloning of Cp149-V124W and HBV Core Protein Purification

The adyw strain of HBV Cp149-pET11c (Genbank accession no. J02202.1) construct was mutated to Cp149-V124W (GTG to TGG) with the QuikChange mutagenesis kit (Stratagene). V124W protein was expressed in *E. coli* BL21 (DE3) in Superior Broth (Athena Enzyme System) with 50 µg/ml carbenicillin at 37° C. overnight. V124W purification was performed as previously described for HBV Cp149-WT purification. Based on the biochemical studies in this paper, in the re-assembly step, using 50 mM NaCl instead of 500 mM NaCl to induce re-assembly yielded more capsid with slightly more aggressive assembly activity. Protein concentration was determined using an extinction coefficient of 70,025 $M^{-1}$ $cm^{-1}$ per V124W dimer at 280 nm, calculated by ExPASy Proteomics Server based on the protein sequence and assuming one disulfide bond per dimer WT dimer was purified exactly as previously described. The extinction coefficient of WT dimer is 60,900 $M^{-1}$ $cm^{-1}$ at 280 nm. Before assembly studies, frozen protein stock was dialyzed into 50 mM HEPES, pH 7.5 for at least 2×2 h at 4° C. The standard assembly buffer was 50 mM HEPES, pH 7.5 at 23° C. with varied NaCl concentrations. Protein stock was treated with 1% to 5% β-mercaptoethanol for 20 min before assembly.

90° Light Scattering

Light scattering was monitored at 90° using 400 inn excitation and emission wavelength with a Photon Technology International fluorometer for at least 800 seconds at 23° C. 10 μM protein (WT or V124W) was incubated with or without 20 μM HAP12 for 20 min prior to adding equal volume of 2× NaCl to a final concentration of 50 mM NaCl. Each sample was repeated 3-4 times independently.

Size Exclusion Chromatography and Calculation of Thermodynamic Parameters

WT and V124W at varied concentrations (WT, 40 to 80 μM; V124W, 2.5 to 30 μM), were induced to assemble at 100 mM NaCl to equilibration for 72 h or longer at 23° C. We judged that 72 h incubation was sufficient for equilibration as longer incubations did not yield more capsid. Capsid and dimer concentrations in assembly reactions were determined by size exclusion chromatography (SEC) through a 21 ml Superose 6 column. $\Delta G_{contact}$ and $K_{D,apparent}$ were calculated as previously described. $K_{D,apparent}$ was the average of the equilibrium dimer concentrations which were nearly constant.

HAP12 Titration of WT and V124W Assembly

To test for resistance to HAP molecules, 10 μM protein with varied HAP12 concentrations (2.5 to 60 μM) was induced to assemble at 50 mM NaCl. Before adding 10× NaCl, protein was incubated with HAP12 at 23° C. for 20 min. Each reaction was incubated at 23° C. for 24 h to equilibrate. Under these conditions, 24 h was long enough to allow reactions to reach equilibrium. Capsid, abnormal structures and dimer concentrations were determined by SEC as described above. HAP12 absorbance was subtracted in the calculation of WT aberrant structures and dimer concentrations.

Transmission Electron Microscopy

Samples from light scattering experiment were diluted to 3.5 μM, applied to glow-discharged carbon copper grids (EM Sciences), and negatively stained with either 2% uranyl acetate or 1% ammonium molybdate. Micrographs were taken at a nominal magnification of 40,000× on a 4K×4K CCD camera (Gatan) using a JEOL-1010 transmission electron microscope.

Cell Cultures and Transfections

All HBV plasmids used in cell culture experiments were derived from subtype ayw (Genbank accession no. V01460). These plasmids express pgRNA under the control of the cytomegalovirus (CMV) immediate early promoter. Plasmids $WT^{P+C+}$ and $V124W^{P+C+}$ express pgRNA, reverse transcriptase (P), WT or V124W core (C) and X proteins, but do not express envelope proteins. Plasmids $C^{WT}$ or $C^{V124W}$ express core protein but not P or envelope proteins and lack a functional encapsidation signal, GFP protein was expressed from a separate plasmid (provided by Bill Sugden, UW-Madison). Details of construction and sequence of any plasmid will be provided upon request.

The human hepatoma cell line Huh7 was used to study HBV replication. Cells were grown in 60 mm plates at 37° C. in 5% $CO_2$, in DMEM/F12 medium supplemented with 5% FBS (Invitrogen, Grand Island, N.Y.). Cells were approximately 75% confluent or greater at time of transfection. DNA transfections were performed using calcium phosphate precipitation. For experiments using $WT^{P+C+}$ and $V124W^{P+C+}$, 5 μg of total plasmid mass was transfected. Each transfection experiments were repeated three times independently. For V124W titration experiment, 2 μg $WT^{P+C+}$ and varied $C^{V124W}$ (0 to 8 μg) was used. A filler plasmid pCMV-Sport6 was used to keep the total plasmid mass at 10 μg. 0.125 μg of the GFP expression plasmid was used in every transfection. Typically, medium containing the calcium phosphate precipitate was removed after 16 hours, fresh medium added, and the cultures were grown for an additional 96 hours.

Isolation of Proteins and Encapsidated DNA

Nucleic acid from cytoplasmic capsids was isolated as described previously. Briefly, cells were lysed in a solution containing 50 mM Tris, 1 mM EDTA, 0.2% NP40, pH 8.0. Nuclei were pelleted via centrifugation and supernatant was collected. A fraction of this lysate was used for detection of core protein and GFP. The remainder of the cytoplasmic lysate was treated with 45 units of micrococcal nuclease (Worthington Biochemicals, Lakewood, N.J.) in the presence of 2 mM $CaCl_2$ to digest plasmid DNA and unencapsidated pgRNA, followed by treatment with 0.4% SDS and 0.4 mg/ml Pronase® (Roche, Nutley, N.J.) to digest nucleocapsids and P protein. Encapsidated nucleic acids were extracted with 1:1 phenokchloroform, precipitated with ethanol and NaCl, and re-suspended in 30 μl of a solution of 10 mM Tris, 0.1 mM EDTA, pH 8.0.

Western Blot Analysis of Core Protein and GFP

A fraction of cytoplasmic lysate was used to run a 15% SDS-PAGE, followed by transfer of proteins to PVDF-FL (Millipore®, Billerica, Mass.) in methanol transfer buffer (details of SDS-PAGE and transfer solutions provided upon request). Blocking was done in Li-Cor® Blocking Buffer diluted 1:1 with 1×PBS. Antibody preparations were made in the same solution, with the addition of Tween-20® to a final concentration of 0.2%. Core protein was detected using a rabbit α-core antibody (Austral Biologicals®, San Ramon, Calif.) at a dilution of 1:500, and a goat α-rabbit IRDye800CW antibody (Li-Cor®) at a dilution of 1:10,000. GFP was detected using a mouse α-GFP antibody (Santa Cruz® Biotechnology, San Cruz, Calif.) at a dilution of 1:500, and a goat α-mouse IRDye680LT antibody (Li-Cor®) at a dilution of 1:10,000. Imaging of membranes was performed on a Li-Cor® Odyssey® instrument. Core levels were normalized to GFP levels for quantitation. Student's t-test was used to test the difference of the core levels in different transfections.

Southern Blot Analysis of Encapsidated DNA

An aliquot of viral DNA was electrophoresed through a 1.25% agarose gel. DNA was denatured and neutralized in situ in 0.5 N NaOH/1.5 M NaCl and 1 M Tris/1.5 M NaCl, respectively, followed by passive transfer to Hybond-N (GE® Lifesciences, Piscataway, N.J.) in 10×SSC. Viral DNA was detected on the membrane using an equimolar pool of oligonucleotides that detected (−) DNA. 10 pmol of this pool was labeled 5' with P32[γ]-ATP using T4 polynucleotide kinase (NEB®, Ipswitch, Mass.), and added to the membrane in 15 ml of Church hybridization buffer. Hybridization was performed overnight at 48° C. Membranes were washed in Church wash buffer 5-6 times at room temperature. Autoradiography was performed using a Typhoon 8600 PhosphorImager (Molecular Dynamics). Levels of DNA were measured using the software ImageQuant® 5.2 (Molecular Dynamics). DNA levels were normalized to GFP levels as determined previously by western blot.

Result and Discussion

Using structural and biochemical methods we are able to identify an assembly effector's binding site on a given virus' core protein. In the case of HBV, the following article is incorporated fully in this application to show the material and method used to identify the binding pocket of HAP on HBV core protein: Small-Molecule Effectors of Hepatitis B Virus Capsid Assembly Give Insight into Virus Life Cycle (*J Virol* 82, 10262-10270).

Briefly, based on a low-resolution crystal structure of a capsid-HAP complex, a closely related series of HAPs were designed and synthesized. These HAPs differentially strengthen the association between neighboring capsid proteins, alter the kinetics of assembly, and give rise to aberrant structures incompatible with a functional capsid. In the crystal structure with bound HAP, the HAP antiviral was only found in the C subunit at the C-D interface (FIG. 1, right). In the FIG. 1, bound HAP is a space-filing model (yellow), the C subunit shows a surface shaded (green) and the incoming D subunit is a ribbon diagram (purple).

HBV Cp149-V124W Assembles Better Than Wild Type Cp149 in Terms of Kinetics and Thermodynamics.

90° Light scattering is a well-established method to monitor the virus assembly kinetics because of the significant difference between the size of the capsid and the dimer. HBV core protein assembly is induced by increasing the ionic strength in vitro, which is achieved by adding NaCl to the reaction system. Higher ionic strength leads to assembly faster and further due to the stronger association energy between dimers.

As shown in FIGS. 6A and 6B, 10 μM Cp149-V124W assembles at 50 mM NaCl, where 10 μM wild type Cp149 does not assemble at all. Even at 150 mM NaCl, we did not observe any capsid formation for 10 μM wild type Cp149 (data not shown). The low ionic strength required for assembly of Cp149-V124W indicates that the association energy in the Cp149-V124W dimer interface is stronger than the wild type Cp149 dimer. In the presence of excess amount of HAP12 (2 HAP12 per dimer), 10 μM wild type Cp149 assembly kinetics at 50 mM NaCl becomes very fast. The light scattered increases rapidly after adding NaCl. The high light scattering signal is due to the formation of large abnormal structures in the presence of HAP12. However, at the equal amount of protein and HAP12 concentration, the kinetics of the Cp149-V124W assembly at 50 mM NaCl is not affected as much as the wild type Cp149 assembly (FIG. 6B), which indicates that the Cp149-V124W is HAP12 resistant to some extent, though not completely resistant. The fast kinetics and HAP resistance of Cp149-V124W is consistent with our prediction that Cp149-V124W behaves like the HAP-bound Cp149.

Size exclusion chromatography quantitatively determined the assembly products. As shown in FIG. 6, there is no assembly of 10 μM wild type Cp149 at 50 mM NaCl 23° C., while about 50% Cp149-V124W dimers assemble into capsids under the same condition. Excess amount of HAP12 helps wild type Cp149 assembles into larger non-capsid structures rather than normal capsid, which elute earlier than capsid through the Superrose 6 column. The more HAP12 we added, the earlier the non-capsid peak eluted. HAP12 does not change Cp149-V124W assembly thermodynamics greatly compared to wild type Cp149. 60 μM HAP12 improved 10 μM Cp149-V124W assembly by 20%, while under the same condition, wild type Cp149 assembly was enhanced from no assembly without HAP12 to 95% assembly with 60 μM HAP12 (FIG. 6C). Though HAP12 has a small effect on Cp149-V124W assembly thermodynamics, we still observed the capsid peak shifting with the increasing amount of HAP12. The shifting in Cp149-V124W assembly with HAP12 is not like the case in wild type Cp149. Because the capsid peak is always of mixture of T=4 and T=3 capsids in HBV assembly, we think the binding of HAP12 to Cp149-V124W changes the ratio of T=4 and T=3 capsids during assembly. Thus, the HAP12 bound Cp149-V124W favors the T=4 capsid formation (FIG. 11 and FIG. 12).

Capsid assembly is an entropy driven process which is temperature and ionic strength dependent. Based on the thermo-parameter calculation, the association energy of Cp149-V124W dimer-dimer interface is much stronger than the wild type Cp149. At 23° C. 100 mM NaCl, the calculated $\Delta G_{cont}$ for Cp149-V124W is −3.73±0.13 kcal/mol, while the $\Delta G_{cont}$ for wild type Cp149 is −2.74±0.04 kcal/mol at the same condition. The pseudo-critical concentration of wild type Cp149 at 100 mM NaCl 23° C. is 43.6±5.1 μM, while the pseudo-critical concentration of Cp149-V124W is 1.43±0.56 μM in the same condition. This surprisingly small pseudo-critical concentration of Cp149-V124W indicates an aggressive assembly mutant (FIG. 10 and Table 3).

HBV Cp149-V124W Assembly Produces Normal Capsids with and without HAP12.

Figure 7:
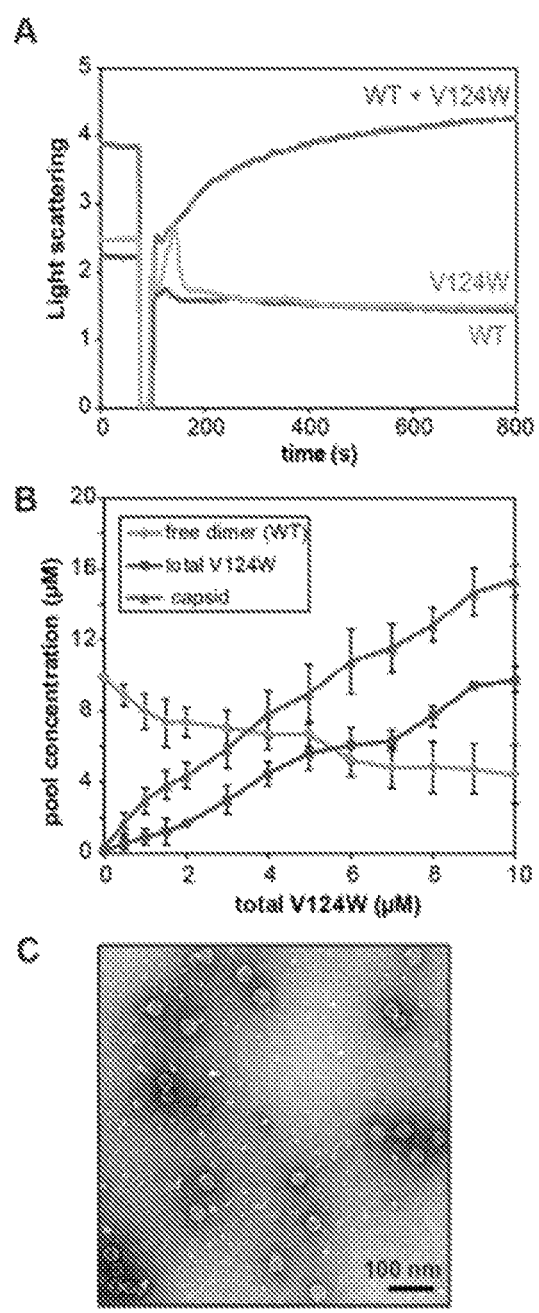
FIG. 7. WT and V124W dimers co-assembled into capsids in vitro. (A) Co-assembly kinetics of 10 µM WT and 1 µM V124W induced by 100 mM NaCl, 23° C. was monitored by 90° light scattering. 10 µM WT and 1 µM V124W alone did not assemble under these conditions. However, if the two proteins were mixed together, time-dependent co-assembly kinetics were observed. Each light scattering trace was an average of four independent experimental results. (B) Co-assembly thermodynamics at 100 mM NaCl, 23° C. In the absence of V124W, 10 µM WT dimer did not assemble. With increasing V124W, free WT dimer concentration decreased and the yield of capsids increased. The total capsid concentration exceeded the total concentration of V124W, indicating co-assembly. Each point is an average of three to five independent experiment results. (C) Negatively stain electron micrographs of 10 µM WT and 5 µM V124W co-assembly products. No aberrant structures were observed. Scale bar represents 100 nm.

The abnormal structures in wild type Cp149 assembly with HAP12 were identified by transmission electron microscope (FIG. 14). We observed large closed and open structures with diameter ranging from about 40 nm to 80 nm for wild type Cp149 assembly with HAP12. HAP12 binds to the HBV core protein dimer interface and changes the assembly geometry by stabilizing the six-fold arrangement and destabilizing the five-fold arrangement. Though we think Cp149-V124W mimics the HAP-bound Cp149, we only observed normal capsids in Cp149-V124W assembly both with and without HAP12, and no abnormal structures at all (FIGS. 14, 15 and 7C). Even if HAP12 binds to Cp149-V124W weakly, HAP12 does not change the capsid assembly geometry enough to produce the abnormal structures.

HBV Cp149-V124W Assembly Leads to Kinetic Trap at Moderate to High Ionic Strength.

HBV capsid assembly is a polymerization process of core proteins, starting from the nucleation of dimers to form trimer of dimers, followed by a rapid elongation process to complete the capsid. The weak dimer-dimer association energy is the driving force for virus assembly. The binding of HAP to the dimer interface improves this weak interaction and changes the assembly geometry, leading to fast kinetics and abnormal structures. Without HAP, 30 μM wild type Cp149 only assembles into normal capsid at moderate to high ionic strength (300 mM to 500 mM NaCl) (FIG. 11, far right). However, 30 μM Cp149-V124W, which has stronger dimer-dimer interaction, assembles into kinetically trapped intermediates at moderate to high ionic strength (FIG. 11, 50 mM to 500 mM NaCl). From the sucrose gradient centrifugation, we observed that at 50 mM NaCl, 30 μM V124W assembles into mostly T=3 capsid; with the increasing of NaCl concentration above 100 mM NaCl, the assembly products become smaller and smaller, which seem to be kinetically trapped intermediates (FIG. 11).

The average molecular weight of kinetically trapped intermediates in Cp149-V124W assembly is determined by multi-angle laser light scattering (MALLS) (FIG. 13). The estimated wild type Cp149 dimer molecular weight is 40 kDa. Though it is 17% off the actual molar weight, 34 kDa, it is still a reasonable estimation since MALLS result is not sensitive for small molecules. For wild type Cp149 assembly at 500 mM NaCl, the average mass of the capsid fraction is consistent at 3.5 MDa, which corresponds to a mixture of T=3 and T=4 capsids. While for Cp149-V124W assembly from low to high NaCl concentration, the average molar weight at the capsid fraction varies from 3 MDa to 1.5 MDa, indicating the existence of assembly intermediates. The fraction elutes at 7.5 ml is large aggregation during assembly, which happens in both wild type Cp149 and Cp149-

V124W assembly. At the capsid fraction, ~9 ml, we see the refractive index becomes smaller and shifts to larger volume with the increasing of NaCl concentration in Cp149-V124W assembly, consistent with the prediction that assembly is kinetically trapped. Interestingly, at the dimer fraction, 17-18 ml, we see the wild type Cp149 dimer elutes about 0.35 ml earlier than Cp149-V124W dimer. This is probably due to the different conformation between these two dimers. Cp149-V124W may adapt a relatively compact conformation, which is more easily to be activated and/or partially activated. We have also noticed that there is small intermediate and/or nuclei accumulated around the dimer fraction during Cp149-V124W assembly. The higher the ionic strength, the more the accumulated intermediates. This is also a good evidence of kinetic trap.

HBV Cp149-V124W Confers High Resistance to HAP12.

The HAP12 titration on Cp149-V124W assembly shows the binding affinity of HAP12 to Cp149-V124 is extremely weak. Excess amount of HAP12 drives wild type Cp149 assembly significantly further, from no assembly to almost 95% assembly at 60 μM HAP12 (FIG. 6C). However, the same amount of HAP12 does not affect the extent of Cp149-V124W assembly greatly. As shown in FIG. 6C, 10 μM Cp149-V124W dimer assembly is improved by 20% at 60 μM HAP12. This weak binding affinity of HAP12 for Cp149-V124W demonstrates that Cp149-V124W has high resistance for HAP12.

The preferred approach to detect co-assembly is to demonstrate that the less assembly-proficient protein (e.g. Cp149) can participate in assembly of the more active protein (e.g. Cp149-V124W). Typically 50% of 10 μM Cp149-V124W assembles when 50 mM NaCl is added to it; under similar conditions, 45 μM Cp149 is need to see any assembly (FIG. 10). For co-assembly, 10 μM Cp149-V124W dimer, is mixed with varying concentrations of Cp149 all in a low salt buffer. The NaCl concentration is then raised to 50 mM, which will initiate Cp149-V124W assembly but have no effect on assembly of Cp149. Assembly is assayed by light scattering and/or by size exclusion chromatography (SEC). Co-assembly is indicated by increased light scatter or yield of capsid by SEC. A more sensitive assay is to use about 5 μM Cp149-V124W, slightly below the pseudo-critical concentration of assembly, so that detectable capsid requires initiation and stabilization of assembly by Cp149-V124W and participation of Cp149 to provide the chemical activity needed to influence the detailed balance of mass action.

Hypothetically, it is possible for an assembly-hyperactive mutant to exclude the weaker binding wild type from assembly. This may occur when assembly conditions are so low in ionic strength that the wild type protein is essentially locked in an assembly-inactive state and even the induced fit effect is inadequate to allow it to participate in assembly. For this reason, the strongest dominant negative effect is unlikely to be associated with the strongest assembly-activating mutation.

We also found that HBV capsid assembly is allosterically regulated. In allostery-regulated assembly, the free dimer undergoes a conformational change to become competent to nucleate and participate in assembly. V124W has stronger association energy at the dimer-dimer interface compared to WT. Since nucleation is the rate-limiting step in capsid assembly, this stronger dimer-dimer interaction could lead to more stable nuclei, which would in turn produce more capsid. Indeed, HAP molecules increased assembly kinetics by favoring the assembly active states. We found that V124W, which assembles very rapidly compared to WT, adopts a relatively more compact conformation as shown by SEC elution (FIG. 6B) SEC separates particles based on Stokes radius; the slower elution of V124W indicated conformational differences between WT and V124W dimers. Usually the WT dimer in a capsid has a more compact conformation compared to the free dimer, thus the assembly behavior of V124W is consistent with its structural feature. The free dimer structure, based on the crystal structure of assembly-incompetent Y132A dimer, had substantive conformational differences. In solution this protein favored, on average, a less compact structure than WT based on its elution from SEC which is sensitive to a protein's Stokes' radius. Thus, these data support that HBV core protein dimers undergo allosteric changes associated with assembly activity and that HAPs favor the assembly-active state.

As shown in the electron micrographs V124W did not assemble into large aberrant structures, which was unlike HAP-induced WT assembly products (FIG. 15B). Similarly, phenylpropenamides bind to the same site at the dimer-dimer interface and change the tertiary structure but do not affect the global capsid structure. Even at low HAP to dimer stoichiometries, normal capsids were observed. Indeed, using pure BAY41-4109, it has been shown that greater than one HAP per two dimers is necessary to generate aberrant structures. This indicates that V124W dimers repel HAP and prevent further HAP binding, making V124W HAP resistant. It is also consistent with the conclusion that V124W is a de facto HAP bound mutant, once it is in de facto HAP bound status, the conformation of the mutant makes HAP binding-less possible.

More broadly speaking, any viral mutation that makes HAP binding less possible but displays similar conformation of de facto HAP bound protein status is destructive to viral reproduction due to its dominant negative assembly feature similar to V124W This in turn proves the antivirus power of assembly effectors, or any mutations that can mimic assembly effectors function.

In the HAP12 titration experiment shown in FIG. 6 we observed that V124W capsid eluted later than WT capsid and with increasing HAP12 concentration V124W capsid peak eluted earlier. It's possible that V124W assembled so aggressive that large intermediates, which were close to but smaller than the capsid size, might exist. There is no evidence that <50 μM HAP12 leads V124W to the massive aberrant structures seen in WT assembly, as V124W capsid did not elute in the void volume in SEC (FIG. 6B) and migrated as a well-demarcated band in sucrose gradients (FIG. 12). We observed capsid-like particles and broken capsids by TEM in V124W assembly with 60 μM HAP12 (FIG. 15). Since HAP12 has a weak binding affinity for V124W, it's likely that the effect of HAP12 on V124W quaternary structure is not as much as on WT.

Assembly effectors such as HAPs and phenylpropenamides have been suggested as antiviral-agents. A caveat to their use as a therapy would be potential emergence of resistant mutants. We have demonstrated that V124W dimer is HAP-resistant. HAP12 only modestly affected V124W assembly kinetics and thermodynamics. Unfortunately, from the virus's perspective, the V124W acts like WT in the presence of an assembly effector in biochemical studies (FIGS. 5 and 6). In cell culture, the phenotype of expression of V124W is similar to the effects observed for HAP treatment (FIG. 9A). Therefore, the resistance to HAP12 conferred by V124W, or any other mutations similar to V124W phenotype is destructive to infection and may not be a pathway to viral escape of HAPs, phenylpropenamides, or other assembly effectors.

The chemical nature of the HAP variants correlated well with the structure of the HAP binding pocket. The thermodynamics and kinetics of in vitro assembly had strong and predictable effects on product morphology. However, only the kinetics of in vitro assembly had a strong correlation with inhibition of HBV replication in HepG2.2.15 cells; there was at best a weak correlation between assembly thermodynamics and replication. The correlation between assembly kinetics and virus suppression implies a competition between successful assembly and misassembly, small molecule induced or otherwise.

Based on this model, example 2 and 3 are contemplated and carried out to identify dominant negative core protein to deplete normal core protein, therefore inhibit effective virion production.

Example 2. Core Protein Mutant's Ability to Co-Assemble in Vitro and in Cells With the model of HAP binding to Core protein illustrated in FIGS. 1 and 4, we generated more mutants of subunit D, with a focus on V124W first, to show that filling the HAP pocket with mutated V124 has some kinetic effects on assembly. We have shown that V124W drops the threshold concentration for assembly by about 50 fold and dramatically speeds up assembly. The V124W expression in cells results in HAP-like behavior including faster and further assembly of wild type capsid proteins, suppressed DNA and protein expression level, and other virus inhibition. See FIG. 9. We have shown that mutated and wild type Cp can co-assemble in vitro.

Determining Co-Assembly In Vitro

Co-assembly in vitro, with purified proteins, is diagnostic for the potential for a dominant negative phenotype. This assay tests for the ability of an assembly-hyperactive mutant to (i) interact with wild type protein and (ii) to nucleate assembly of wildtype protein. Because the full length, 183 amino acid core protein (Cp183) is difficult to work with in vitro, because of its poor solubility, these experiments are performed with the 149 amino acid core protein assembly domain Cp149 and mutants thereof.

Based on the previous study with HAPs, we designed a single amino acid mutation (V124W) in the HAP binding pocket which partially fills in the HAP binding site (FIG. 4). We expect to see the HAP-mimic behavior with this mutant, and at the meantime, this mutant should confer some extent of resistance to HAP molecules since the binding site is partially occupied.

Among the most well studied HAPs, HAP12 is one of the strongest HBV capsid assembly-effector. HAP12 can increase the association energy at the Cp149 dimer interface by 1.92 kcal/mol at 150 mM NaCl 37° C., which is a significant improvement considering the weak association energy at the dimer interface, −3.87 kcal/mol. The binding of HAP12 to wild type Cp149 can induce the assembly at very low ionic strength, where wild type Cp149 does not assemble without HAP12 (FIG. 6A) since the pseudo-critical concentration is extremely high (FIG. 10). HAP12 also induces the formation of abnormal structures in wiltype HBV capsid assembly (FIG. 14). In this study, we choose HAP12 as the probe to test the resistance of Cp149-V124 to HAP molecules. The resistance of Cp149-V124W to HAP12 will provide us the most information about the mutant's resistance to HAPs.

The single amino acid mutation (V124W) was made on the assembly domain of HBV core protein (Cp149), which is the N-terminal first 149 residues of the core protein. Wild type Cp149 has been shown to be able to assemble into capsid properly in vitro. Using wild type Cp149 as a control, we found that Cp149-V124W assembles much faster and further than the wild type Cp149 (FIGS. 5 and 6); Cp149-V124W is resistant to HAPs compared with the wild type Cp149; Cp149-V124W assembly favors different capsid geometry (FIG. 11 and FIG. 12).

The co-assembly experiments showed that V124W interacted with WT and could thus have a dominant negative effect, analogous to the antiviral effects of low concentrations of HAPs. Co-assembly studies showed that V124W could enhance WT assembly like HAP molecules (FIG. 7). Since V124W was more assembly-active than WT, we speculated that V124W nucleated assembly more readily than WT, so that during elongation WT or V124W could both contribute to assembly. By enhancing association, the behavior of V124W is consistent with increased buried hydrophobic surface; yet, the observation of morphologically normal capsids (FIG. 7C) argues that it does not grossly disturb the dimer interface. Thus, addition of V124W or modest concentrations of HAP to an assembly reaction results in nearly identical behavior (FIG. 6B).

Similar to the FLAP-like behavior in the co-assembly studies, cell culture studies showed that V124W inhibited viral genome replication in a dominant negative manner. Consider capsid formation in a WT infection: core proteins assemble around pgRNA-reverse transcriptase complex to form an RNA-filled capsid. In the capsid, pgRNA is reverse transcribed to (−)DNA and then the (+)DNA is synthesized. In our cell culture system, surface proteins were not expressed so that capsids were not secreted.

HBV DNA synthesis in the presence of V124W did not correlate with the level of expression of core protein. When V124W and WT were co-expressed at a 1:1 ratio, the total core protein accumulation was not affected by V124W, though the DNA synthesis was profoundly suppressed. In the V124W titration experiment, when different amounts of V124W core plasmid were co-transfected with WT expression plasmid, the suppression effect of expressing V124W core protein was very much like the effect of adding HAP molecules to cell culture. In the future, we are able to study the antiviral mechanism of HAP molecules by using V124W core protein so that the actual amount of HAP-bound core protein can be controlled. Pure V124W expression led to a >90% reduction in the yield of total DNA, though V124W protein accumulation was only suppressed by 40%.

In sum, we designed a novel HBV core protein mutant that dominantly interferes with HBV replication. When this project was started, we only had a 5 Å structure for guidance. Based on HAP-resistance we confirmed the putative HAP binding site. An independent study shows that phenylpropenamides bind the same pocket, accentuating the importance of the dimer-dimer interface for regulating assembly.

Assembly effectors have great potential as antiviral drugs. As development of assembly effectors is in its infancy, this study is the first example of examining resistance to their action. We observe that resistance to HAPs through the mutations in the HAP binding pocket would be destructive to the virus. Mutations that affect the HAP binding pocket provide new opportunities to study capsid assembly; use of the HBV capsid-HAP structure to design these mutations is an example of the power of chemical biology.

Method for Determining Dominant Negative Effect in Cultured Cells

Co-expression of HBV and an assembly-hyperactive mutant in cultured hepatoma cells tests for dominant negative effect under conditions that are similar to those in an infected liver. An assay for virus replication is Southern blotting of intracellular DNA genomes. In this assay, Huh7 or HepG2 cells are transfected a plasmid that expresses HBV. Depending on the assay, the HBV genome may or may not allow expression of the surface proteins. The mutant core protein is expressed from a second expression plasmid that contains mutations ablating production of the other viral proteins.

A 60 mm plate nearing confluency with either Huh7 or HepG2 cells is co-transfected by the calcium phosphate method with a mixture of 2 μg of the wt HBV expression plasmid, 8 μg of the Cp149-V124W expression plasmid, and 0.5 μg of a GFP-expressing plasmid (a control for transfection efficiency). Four days post-transfection, cells are lysed, treated with micrococcal nuclease to remove unencapsidated nucleic acid. The cores in the lysate are then treated with pronase, phenol extracted, and the released DNA run out on a 1.25% agarose gel and Southern blotted. In control reactions, without the dominant negative mutant, bands are visible for the minus strand (SS), double-stranded linear genomes (DL), and the mature relaxed circular DNA of infectious virions (RC). To assay for accumulation of core protein, lysate is resolved by SDS-PAGE and Western blotted.

Using an HBV genome with intact surface protein expression, secreted virus can be determined by collecting media four days post transfection, running a sample through a native 1% agarose gel, and assaying by Western and or Southern blot of the virion band.

FIG. 9 shows V124W acts as a dominant negative in Huh7 cells. Briefly, Huh7 cells were co-transfected by:

- a HBV expression plasmid (deficient for envelope protein expression) and
- one of the following core expression plasmids (only expresses core protein):
  - WT core
  - V124W
  - empty plasmid Four days post-transfection, intracellular encapsidated DNAs were isolated and Southern blotting was performed to detect (−) DNA. As FIG. 9A indicates V124W expression profoundly suppressed viral DNA synthesis. WT and V124W lanes were shown in duplicates. Mock transfection did not express any HBV proteins. FIG. 9B shows Quantification of Southern blot data from three independent transfections. WT yields of rcDNA, dlDNA, ssDNA and total DNA were normalized to 100%. Yields of DNA in transfections with V124W, exclusively, were 3-7% of WT. Co-transfections of WT and V124W yielded 8-37% of the DNA in WT pools (Table 1). FIG. 9C shows western blot of core protein level in WT, V124W and co-transfection experiments. FIG. 9D shows quantification of western blot data from three independent transfections. V124W core protein yield was statistically less than WT (indicated by the star). However, there was no statistical difference between the core protein levels in 1:1 co-transfection and WT transfection alone (Table 2). FIG. 9E shows V124W titration of WT expression in Huh7 cells. With increasing V124W core protein expression, WT DNA synthesis was suppressed.

In V124W transfected cells, no visible RC and DL DNA and very little SS DNA were present compared to WT transfection or empty vector alone transfection, showing V124W's dominant negative effect to wipe out (The Surfaris) any other wild type encapsidated DNA genome.

Other mutants and double mutants as listed in Example 1 for enhanced efficacy in vitro and in culture will be conducted following the similar approach and identify the dominant negative effect of these mutants.

Example 3. Gene Therapy by HBV Cpdominant1 Dominant Negative Activity in Mice Next we will move HBV Cpdominant1 into an AAV vector according to the following article: Optimisation of Self-complementary AAV Vectors for Liver-directed Expression Results in Sustained Correction of Hemophilia B at Low Vector Dose. *Molecular Therapy* vol. 16 no. 2 February 2008. The material and method of constructing scAAV-FIX liver specific gene delivery system in this article and the significance of using scAAV as a safety gene delivery vector are fully incorporated into this application. Self-complementary adeno-associated virus (scAAV) significantly minimizes the vector load required to achieve sustained transgene expression. The ability of low dose scAAV-FIX vectors to achieve near-physiological expression in liver cells prompts us to insert HBV Cpdominant1 into scAAV-FLX liver expression cassette to deliver dominant negative HBV Cpdominant1, therefore to achieve liver-directed gene delivery.

Briefly, HBV Cpdominant1 nucleotides as set forth in SEQ. ID. NO: 40 are to be inserted into scAAV-FIX cassette to stably express Cpdominant1 in HBV infected mice's liver cells. Liver cell extracts are analyzed according to the protocol outlined in Example 2 with modification to comply with animal experiment procedures, to determine the effect of dominant negative mutation Cpdominant1 in livers infected with HBV. The predicted result will indicate transfection of scAAV-FIX Cpdominant1 results less or none effective HBV virion packaging, fast clearance of any existing hybrid virion (Cpdominant/Cp wt) and empty virion, and/or reduced or none (−) HBV DNA genome in intracellular extract, etc.

Example 4. Method for Determining Relative Concentrations of Wildtype and Dominant Negative Forms of Core Protein It is often useful to know the relative concentration of the dominant negative mutant in relation to the concentration of core protein from the viral infection. This can help determine the relative dose of dominant negative required for suppression of virus. In HBV it has been shown that truncation of Cp to residue 172 or 176 results in a core protein that is able to produce particles that support reverse transcription at levels indistinguishable from those supported by the full-length Cp. However, the truncated Cp is readily distinguished from the full-length protein by western blot. This method is applicable whether the source of the dominant negative genome is transfection or a gene therapy vector and whether the virus producing system is cell culture, animal, or human.

Example 5. Design HIV Capsid CA Mutations that Mimic Small Molecule Assembly Effector In this example, a class of small molecule antiretroviral compounds that targets HIV-1 capsid (CA) assembly via direct binding to the N-terminal domain (NTD) of CA has shown broad spectrum of antiviral effect that correlates with its ability to increase the rate of CA multimerization in vitro. A crystal structure of the compound in complex with HIV-1 CA protein (PDB accession 2XDE) reveals a novel binding pocket (FIG. 6) in the N terminal domain of the protein.

Mutations in HIV CA confer resistance to several members of the small molecule assembly effector. EM analysis shows the small molecules profoundly affect the morphology of nascent HIV particles.

Based on virus assembly kinetics and computer modeling, mutations proximal to the PF3450074 binding pocket might destabilize or enhance the stability of viral cores and result in specific postentry defects in virus replication. Superpositioning assembled capsid structures with the structure of the PF 3450074/CA complex was generated in FIG. 17A. In highlighted residues of FIG. 17B, any mutation that mimics the effect of PF3450074 on CA assembly rate, but renders the mutant resistant to the small molecule assembly effector is a good candidate of dominant negative mutant to provide broad antiviral effect to HIV replication.

It should be understood that the foregoing relates to exemplary embodiments of the disclosure and that modifications may be made without departing from the spirit and scope of the invention as set forth in the following claims.

---

The invention claimed is:

1. A method to identify an antiviral protein or polypeptide having a dominant negative mutation, the method comprising:
    a. providing to a wild type virus a small molecule assembly effector that affects wild type virus assembly;
    b. identifying said small molecule assembly effector's binding pocket on a wild type viral structural protein of the wild type virus;
    c. performing site-directed mutagenesis at the identified assembly effector's binding pocket on the wild type viral structural protein to obtain a mutant structural protein or polypeptide with at least one amino acid mutation and a filled binding pocket;
    d. testing said mutant structural protein or polypeptide's self-assembly kinetics in the absence of a viral assembly signal and in the absence of a small molecule assembly effector;
    e. testing said mutant structural protein or polypeptide's ability to co-assemble with wild type virus structural proteins in the absence of viral assembly signal and in the absence of a small molecule assembly effector; and
    f. selecting as the antiviral protein or polypeptide a mutant structural protein or polypeptide with accelerated self-assembly kinetics that co-assembles with and causes accelerated assembly of wild type virus structural proteins in the absence of viral assembly signal and in the absence of a small molecule assembly effector.

2. The method of claim 1, wherein said wild type virus is selected from the group consisting of: Hepatitis B virus (HBV), Flaviviridae, Togaviridae, Retroviridae, Herpesviridae, and Papillomaviridae.

3. The method of claim 1, wherein said virus is Hepatitis B virus (HBV) and said small molecule assembly effector is a heteroaryldihydropyrimidine (HAP) or phenylpropenamide.

4. The method of claim 1, wherein said virus is Hepatitis B virus (HBV) and said binding pocket is located at the interface between subunits of HBV core protein.

5. The method of claim 1, wherein said mutagenesis occurs on Hepatitis B virus (HBV) core protein V124.

6. The method of claim 1, wherein said virus is human immunodeficiency virus (HIV) and said small molecule assembly effector is selected from the group consisting of: PF01385801, PF-3450074, and PF-3759857.

7. The method of claim 1, wherein said mutagenesis occurs on the CA domain or SP1 domain of human immunodeficiency virus (HIV) Gag protein.

8. A hepatitis B virus core protein comprising a V124W mutation as set forth by SEQ ID NO: 1.

9. A method of preparing an antiviral protein or polypeptide having a dominant negative effect on replication of a wild type virus, the method comprising:
    a. providing to the wild type virus a small molecule assembly effector that affects wild type virus assembly by binding to a structural protein of the wild type virus, and identifying the small molecule assembly effector's binding pocket on the structural protein;
    b. performing site-directed mutagenesis at the identified small molecule assembly effector's binding pocket on the structural protein to obtain a mutant protein or polypeptide with at least one amino acid mutation and a filled binding pocket;
    c. testing the mutant protein or polypeptide's self-assembly kinetics in the absence of a viral assembly signal and in the absence of a small molecule assembly effector;
    d. testing said mutant structural protein or polypeptide's ability to co-assemble with wild type virus structural proteins in the absence of viral assembly signal and in the absence of a small molecule assembly effector; and
    e. selecting as the antiviral protein or polypeptide a mutant structural protein or polypeptide with accelerated self-assembly kinetics that co-assembles with and causes accelerated assembly of wild type virus structural proteins in the absence of viral assembly signal and in the absence of a small molecule assembly effector.

10. The method of claim 8, wherein said wild type virus is selected from the group consisting of: Hepatitis B virus (HBV), Flaviviridae, Togaviridae, Retroviridae, Herpesviridae, and Papillomaviridae.

* * * * *

SEQUENCE LISTING

```
<160> NUMBER OF SEQ ID NOS: 40

<210> SEQ ID NO 1
<211> LENGTH: 183
<212> TYPE: PRT
<213> ORGANISM: HBV adyw strain

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Trp Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 2
<211> LENGTH: 183
<212> TYPE: PRT
<213> ORGANISM: HBV adyw strain

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60
```

```
Leu Met Thr Leu Ala Thr Trp Val Gly Thr Asn Leu Glu Asp Pro Ala
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Phe Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 3
<211> LENGTH: 183
<212> TYPE: PRT
<213> ORGANISM: HBV adyw strain

<400> SEQUENCE: 3

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Tyr Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 4
<211> LENGTH: 183
<212> TYPE: PRT
<213> ORGANISM: HBV adyw strain

<400> SEQUENCE: 4

Met Asp Ile Asp Pro Tyr Lys Glu Phe Gly Ala Thr Val Glu Leu Leu
 1               5                  10                  15
```

Ser Phe Leu Pro Ser Asp Phe Phe Pro Ser Val Arg Asp Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Leu Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 5
<211> LENGTH: 183
<212> TYPE: PRT
<213> ORGANISM: HBV adyw strain

<400> SEQUENCE: 5

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Ile Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 6

-continued

<211> LENGTH: 183
<212> TYPE: PRT
<213> ORGANISM: HBV adyw strain

<400> SEQUENCE: 6

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Trp
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 7
<211> LENGTH: 183
<212> TYPE: PRT
<213> ORGANISM: HBV adyw strain

<400> SEQUENCE: 7

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Phe
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
            180

<210> SEQ ID NO 8
<211> LENGTH: 183
<212> TYPE: PRT
<213> ORGANISM: HBV adyw strain

<400> SEQUENCE: 8

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Tyr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
            180

<210> SEQ ID NO 9
<211> LENGTH: 183
<212> TYPE: PRT
<213> ORGANISM: HBV adyw strain

<400> SEQUENCE: 9

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

```
Glu Thr Val Leu Glu Tyr Leu Val Ser Phe Gly Val Trp Ile Arg Thr
            115                 120                 125

Pro Pro Ala Tyr Arg Pro Pro Asn Ala Pro Trp Leu Ser Thr Leu Pro
130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 10
<211> LENGTH: 183
<212> TYPE: PRT
<213> ORGANISM: HBV adyw strain

<400> SEQUENCE: 10

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Phe Leu Ser Thr Leu Pro
130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 11
<211> LENGTH: 183
<212> TYPE: PRT
<213> ORGANISM: HBV adyw strain

<400> SEQUENCE: 11

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60
```

```
Leu Met Thr Leu Ala Thr Trp Val Gly Thr Asn Leu Glu Asp Pro Ala
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Tyr Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 12
<211> LENGTH: 183
<212> TYPE: PRT
<213> ORGANISM: HBV adyw strain

<400> SEQUENCE: 12

Met Asp Ile Asp Pro Tyr Lys Glu Phe Gly Ala Thr Val Glu Leu Leu
1               5                  10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Met Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 13
<211> LENGTH: 183
<212> TYPE: PRT
<213> ORGANISM: HBV adyw strain

<400> SEQUENCE: 13

Met Asp Ile Asp Pro Tyr Lys Glu Phe Gly Ala Thr Val Glu Leu Leu
1               5                  10                  15
```

```
Ser Phe Leu Pro Ser Asp Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Trp Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 14
<211> LENGTH: 183
<212> TYPE: PRT
<213> ORGANISM: HBV adyw strain

<400> SEQUENCE: 14

```
Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Phe Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 15
<211> LENGTH: 183
<212> TYPE: PRT
<213> ORGANISM: HBV adyw strain

<400> SEQUENCE: 15

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Tyr Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 16
<211> LENGTH: 183
<212> TYPE: PRT
<213> ORGANISM: HBV adyw strain

<400> SEQUENCE: 16

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Met Ser Thr Leu Pro
    130                 135                 140

Glu Thr Thr Val Val Arg Arg Arg Gly Arg Ser Pro Arg Arg Arg Thr
```

```
                145                 150                 155                 160
Pro Ser Pro Arg Arg Arg Arg Ser Gln Ser Pro Arg Arg Arg Ser
                    165                 170                 175
Gln Ser Arg Glu Ser Gln Cys
            180

<210> SEQ ID NO 17
<211> LENGTH: 183
<212> TYPE: PRT
<213> ORGANISM: HBV adyw strain

<400> SEQUENCE: 17

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Trp Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Ser
                    165                 170                 175

Gln Ser Arg Glu Ser Gln Cys
            180

<210> SEQ ID NO 18
<211> LENGTH: 183
<212> TYPE: PRT
<213> ORGANISM: HBV adyw strain

<400> SEQUENCE: 18

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Trp Gly Arg
```

```
                    100                 105                 110
Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 19
<211> LENGTH: 183
<212> TYPE: PRT
<213> ORGANISM: HBV adyw strain

<400> SEQUENCE: 19

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Trp Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 20
<211> LENGTH: 183
<212> TYPE: PRT
<213> ORGANISM: HBV adyw strain

<400> SEQUENCE: 20

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
```

```
            50              55              60
Leu Met Thr Leu Ala Thr Trp Val Gly Thr Asn Leu Glu Asp Pro Ala
 65              70              75              80

Ser Arg Asp Leu Val Val Ser Tyr Val Asn Thr Asn Val Gly Leu Lys
                 85              90              95

Phe Arg Gln Leu Leu Trp Phe His Ile Phe Cys Leu Thr Phe Gly Arg
                100             105             110

Glu Thr Val Leu Glu Tyr Leu Val Ser Phe Gly Val Trp Ile Arg Thr
                115             120             125

Pro Pro Ala Tyr Arg Pro Pro Asn Ala Pro Ile Leu Ser Thr Leu Pro
130             135             140

Glu Thr Thr Val Val Arg Arg Arg Gly Arg Ser Pro Arg Arg Arg Thr
145             150             155             160

Pro Ser Pro Arg Arg Arg Arg Ser Gln Ser Pro Arg Arg Arg Arg Ser
                165             170             175

Gln Ser Arg Glu Ser Gln Cys
                180

<210> SEQ ID NO 21
<211> LENGTH: 183
<212> TYPE: PRT
<213> ORGANISM: HBV adyw strain

<400> SEQUENCE: 21

Met Asp Ile Asp Pro Tyr Lys Glu Phe Gly Ala Thr Val Glu Leu Leu
 1               5              10              15

Ser Phe Leu Pro Ser Asp Phe Phe Pro Ser Val Arg Asp Leu Leu Asp
                20              25              30

Thr Ala Ala Ala Leu Tyr Arg Asp Ala Leu Glu Ser Pro Glu His Cys
            35              40              45

Ser Pro His His Thr Ala Leu Arg Gln Ala Ile Leu Cys Trp Gly Asp
        50              55              60

Leu Met Thr Leu Ala Thr Trp Val Gly Thr Asn Leu Glu Asp Pro Ala
 65              70              75              80

Ser Arg Asp Leu Val Val Ser Tyr Val Asn Thr Asn Val Gly Leu Lys
                 85              90              95

Phe Arg Gln Leu Leu Trp Phe His Ile Tyr Cys Leu Thr Phe Gly Arg
                100             105             110

Glu Thr Val Leu Glu Tyr Leu Val Ser Phe Gly Val Trp Ile Arg Thr
                115             120             125

Pro Pro Ala Tyr Arg Pro Pro Asn Ala Pro Ile Leu Ser Thr Leu Pro
130             135             140

Glu Thr Thr Val Val Arg Arg Arg Gly Arg Ser Pro Arg Arg Arg Thr
145             150             155             160

Pro Ser Pro Arg Arg Arg Arg Ser Gln Ser Pro Arg Arg Arg Arg Ser
                165             170             175

Gln Ser Arg Glu Ser Gln Cys
                180

<210> SEQ ID NO 22
<211> LENGTH: 183
<212> TYPE: PRT
<213> ORGANISM: HBV adyw strain

<400> SEQUENCE: 22

Met Asp Ile Asp Pro Tyr Lys Glu Phe Gly Ala Thr Val Glu Leu Leu
```

```
                1               5                   10                  15
Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Met Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 23
<211> LENGTH: 183
<212> TYPE: PRT
<213> ORGANISM: HBV adyw strain

<400> SEQUENCE: 23

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Leu Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

```
<210> SEQ ID NO 24
<211> LENGTH: 183
<212> TYPE: PRT
<213> ORGANISM: HBV adyw strain

<400> SEQUENCE: 24

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Trp Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 25
<211> LENGTH: 183
<212> TYPE: PRT
<213> ORGANISM: HBV adyw strain

<400> SEQUENCE: 25

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Phe Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140
```

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
            180

<210> SEQ ID NO 26
<211> LENGTH: 183
<212> TYPE: PRT
<213> ORGANISM: HBV adyw strain

<400> SEQUENCE: 26

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Tyr Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
            180

<210> SEQ ID NO 27
<211> LENGTH: 183
<212> TYPE: PRT
<213> ORGANISM: HBV adyw strain

<400> SEQUENCE: 27

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

```
Phe Arg Gln Leu Leu Trp Phe His Met Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 28
<211> LENGTH: 183
<212> TYPE: PRT
<213> ORGANISM: HBV adyw strain

<400> SEQUENCE: 28

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Trp Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 29
<211> LENGTH: 183
<212> TYPE: PRT
<213> ORGANISM: HBV adyw strain

<400> SEQUENCE: 29

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Phe Ala Ala Ala Leu Tyr Arg Asp Ala Leu Glu Ser Pro Glu His Cys
            35                  40                  45
```

```
Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 30
<211> LENGTH: 183
<212> TYPE: PRT
<213> ORGANISM: HBV adyw strain

<400> SEQUENCE: 30

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Tyr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 31
<211> LENGTH: 183
<212> TYPE: PRT
<213> ORGANISM: HBV adyw strain

<400> SEQUENCE: 31

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Met Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 32
<211> LENGTH: 183
<212> TYPE: PRT
<213> ORGANISM: HBV adyw strain

<400> SEQUENCE: 32

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Trp Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 33
<211> LENGTH: 183
<212> TYPE: PRT
<213> ORGANISM: HBV adyw strain

<400> SEQUENCE: 33

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Phe Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 34
<211> LENGTH: 183
<212> TYPE: PRT
<213> ORGANISM: HBV adyw strain

<400> SEQUENCE: 34

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Tyr Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
            180

<210> SEQ ID NO 35
<211> LENGTH: 183
<212> TYPE: PRT
<213> ORGANISM: HBV adyw strain

<400> SEQUENCE: 35

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Met Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
            180

<210> SEQ ID NO 36
<211> LENGTH: 183
<212> TYPE: PRT
<213> ORGANISM: HBV adyw strain

<400> SEQUENCE: 36

Met Asp Ile Asp Pro Tyr Lys Glu Phe Gly Ala Thr Val Glu Leu Leu
1               5                   10                  15

Ser Phe Leu Pro Ser Asp Phe Phe Trp Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

```
Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 37
<211> LENGTH: 183
<212> TYPE: PRT
<213> ORGANISM: HBV adyw strain

<400> SEQUENCE: 37

```
Met Asp Ile Asp Pro Tyr Lys Glu Phe Gly Ala Thr Val Glu Leu Leu
1               5                   10                  15

Ser Phe Leu Pro Ser Asp Phe Phe Tyr Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 38
<211> LENGTH: 183
<212> TYPE: PRT
<213> ORGANISM: HBV adyw strain

<400> SEQUENCE: 38

```
Met Asp Ile Asp Pro Tyr Lys Glu Phe Gly Ala Thr Val Glu Leu Leu
1               5                   10                  15

Ser Phe Leu Pro Ser Asp Phe Phe Ser Val Arg Asp Leu Leu Asp
            20                  25                  30

Thr Ala Ala Ala Leu Tyr Arg Asp Ala Leu Glu Ser Pro Glu His Cys
        35                  40                  45
```

-continued

```
Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 39
<211> LENGTH: 183
<212> TYPE: PRT
<213> ORGANISM: HBV adyw strain

<400> SEQUENCE: 39

```
Met Asp Ile Asp Pro Tyr Lys Glu Phe Gly Ala Thr Val Glu Leu Leu
1               5                   10                  15

Ser Phe Leu Pro Ser Asp Phe Phe Leu Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 40
<211> LENGTH: 549
<212> TYPE: DNA
<213> ORGANISM: HBV adyw strain

<400> SEQUENCE: 40

-continued

```
atggacatcg accettataa agaatttgga gctactgtgg agttactctc gtttttgcct      60
tctgacttct ttccttcagt acgagatctt ctagataccg cctcagctct gtatcgggaa    120
gccttagagt ctcctgagca ttgttcacct caccatactg cactcaggca agcaattctt    180 tgctggggg aactaatgac tctagctacc tgggtgggtg ttaatttgga agatccagcg     240
tctagagacc tagtagtcag ttatgtcaac actaatatgg gcctaaagtt caggcaactc    300
ttgtggtttc acatttcttg tctcactttt ggaagagaaa cagttataga gtatttggtg    360
tctttcggat ggtggattcg cactcctcca gcttatagac caccaaatgc ccctatccta    420
tcaacacttc cggagactac tgttgttaga cgacgaggca ggtccctag aagaagaact     480 ccctcgcctc gcagacgaag gtctcaatcg ccgcgtcgca gaagatctca atctcgggaa    540
tctcaatgt                                                            549
```